US009484195B2

(12) United States Patent
Ouyang et al.

(10) Patent No.: US 9,484,195 B2
(45) Date of Patent: Nov. 1, 2016

(54) SYSTEMS AND METHODS FOR TRANSFER OF IONS FOR ANALYSIS

(71) Applicant: Purdue Research Foundation, West Lafayette, IN (US)

(72) Inventors: Zheng Ouyang, West Lafayette, IN (US); Robert Graham Cooks, West Lafayette, IN (US); Sandilya Venkata Garimella, West Lafayette, IN (US); Jason David Harper, Lafayette, IN (US); Nicholas Alan Charipar, Batavia, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/880,613

(22) Filed: Oct. 12, 2015

(65) Prior Publication Data

US 2016/0118237 A1    Apr. 28, 2016

Related U.S. Application Data

(63) Continuation of application No. 14/594,217, filed on Jan. 12, 2015, now Pat. No. 9,159,540, which is a continuation of application No. 14/454,811, filed on Aug. 8, 2014, now Pat. No. 8,963,079, which is a (Continued)

(51) Int. Cl.
*H01J 49/04* (2006.01)
*H01J 49/26* (2006.01)
(Continued)

(52) U.S. Cl.
CPC ......... *H01J 49/0404* (2013.01); *G01N 27/622* (2013.01); *H01J 49/0027* (2013.01);
(Continued)

(58) Field of Classification Search
CPC ............ H01J 49/0404; H01J 49/0027; H01J 49/0031; H01J 49/04; H01J 49/0422; H01J 49/0459; H01J 49/26; H01J 49/40; H01J 49/4215; H01J 49/063; H01J 49/424; H01J 49/0418; H01J 49/049; H01J 49/06; H01J 49/067; H01J 49/165; H01J 49/24; H01J 49/4265; H01J 49/4295
USPC ....... 250/288, 282, 281, 284, 286, 287, 292, 250/285, 289, 396 R
See application file for complete search history.

(56) References Cited

U.S. PATENT DOCUMENTS 4,121,099 A    10/1978 French et al.
4,977,320 A    12/1990 Chowdhury et al.
(Continued)

FOREIGN PATENT DOCUMENTS

WO    2007/138371 A2    12/2007
WO    2008/055667 A2    5/2008
WO    2008/055668 A2    5/2008

OTHER PUBLICATIONS

Extended European Search Report for Application No. 09821010.7 Mailed Nov. 11, 2015 (11 Pages).
(Continued)

*Primary Examiner* — David A Vanore
(74) *Attorney, Agent, or Firm* — Adam M. Schoen; Brown Rudnick LLP

(57) ABSTRACT

The invention generally relates to systems and methods for transferring ions for analysis. In certain embodiments, the invention provides a system for analyzing a sample including an ionizing source for converting molecules of a sample into gas phase ions in a region at about atmospheric pressure, an ion analysis device, and an ion transfer member operably coupled to a gas flow generating device, in which the gas flow generating device produces a laminar gas flow that transfers the gas phase ions through the ion transfer member to an inlet of the ion analysis device.

19 Claims, 19 Drawing Sheets

Related U.S. Application Data continuation of application No. 14/180,915, filed on Feb. 14, 2014, now Pat. No. 8,803,085, which is a continuation of application No. 13/937,913, filed on Jul. 9, 2013, now Pat. No. 8,686,351, which is a continuation of application No. 13/727,840, filed on Dec. 27, 2012, now Pat. No. 8,592,756, which is a continuation of application No. 13/122,651, filed as application No. PCT/US2009/059514 on Oct. 5, 2009, now Pat. No. 8,410,431.

(60) Provisional application No. 61/104,793, filed on Oct. 13, 2008.

(51) Int. Cl.
*H01J 49/00* (2006.01)
*H01J 49/40* (2006.01)
*G01N 27/62* (2006.01)
*H01J 49/42* (2006.01)
*H01J 49/10* (2006.01)

(52) U.S. Cl.
CPC ............ *H01J49/0031* (2013.01); *H01J 49/04* (2013.01); *H01J 49/0409* (2013.01); *H01J 49/0422* (2013.01); *H01J 49/0459* (2013.01); *H01J 49/10* (2013.01); *H01J 49/26* (2013.01); *H01J 49/40* (2013.01); *H01J 49/4215* (2013.01)

(56) References Cited

U.S. PATENT DOCUMENTS

| | | | |
|---|---|---|---|
| 5,412,208 A | 5/1995 | Covey et al. | |
| 5,708,268 A * | 1/1998 | Franzen | H01J 49/063 250/282 |
| 5,739,530 A * | 4/1998 | Franzen | H01J 49/063 250/282 |
| 5,747,799 A * | 5/1998 | Franzen | H01J 49/067 250/282 |
| 5,756,995 A | 5/1998 | Maswadeh et al. | |
| 5,859,433 A * | 1/1999 | Franzen | H01J 49/0404 250/288 |
| 5,873,523 A * | 2/1999 | Gomez | A61M 15/02 239/3 |
| 6,359,275 B1 | 3/2002 | Bertsch et al. | |
| 6,586,731 B1 * | 7/2003 | Jolliffe | H01J 49/049 250/281 |
| 6,649,908 B2 | 11/2003 | Apffel, Jr. et al. | |
| 6,753,523 B1 * | 6/2004 | Whitehouse | H01J 49/005 250/292 |
| 6,818,888 B2 | 11/2004 | Wells et al. | |
| 6,818,890 B1 | 11/2004 | Smith et al. | |
| 6,967,325 B2 | 11/2005 | Smith et al. | |
| 7,066,241 B2 * | 6/2006 | Garimella | F25B 37/00 165/116 |
| 7,078,679 B2 | 7/2006 | Westphall et al. | |
| 7,091,477 B2 | 8/2006 | Jolliffe et al. | |
| 7,098,452 B2 | 8/2006 | Schneider et al. | |
| 7,247,495 B2 | 7/2007 | Amirav | |
| 7,335,897 B2 * | 2/2008 | Takats | H01J 49/142 250/282 |
| 7,405,398 B2 | 7/2008 | Jolliffe et al. | |
| 7,462,822 B2 | 12/2008 | Gebhardt et al. | |
| 7,462,826 B2 | 12/2008 | Schneider et al. | |
| 7,544,933 B2 * | 6/2009 | Cooks | H01J 49/14 250/281 |
| 7,679,053 B2 | 3/2010 | Schneider et al. | |
| 7,700,913 B2 | 4/2010 | Musselman | |
| 7,705,297 B2 | 4/2010 | Musselman | |
| 7,714,281 B2 | 5/2010 | Musselman | |
| 7,838,826 B1 | 11/2010 | Park | |
| 7,910,881 B2 | 3/2011 | Nikolaev et al. | |
| 7,982,183 B2 | 7/2011 | Makarov et al. | |
| 8,008,617 B1 | 8/2011 | Berends, Jr. et al. | |
| 8,084,736 B2 | 12/2011 | Schneider et al. | |
| 8,148,679 B2 | 4/2012 | Makarov et al. | |
| 8,148,680 B2 | 4/2012 | Makarov et al. | |
| 8,242,440 B2 | 8/2012 | Splendore et al. | |
| 8,309,916 B2 | 11/2012 | Wouters et al. | |
| 8,330,119 B2 * | 12/2012 | Chen | H01J 49/0431 204/230.2 |
| 8,410,431 B2 * | 4/2013 | Ouyang | H01J 49/0404 250/281 |
| 8,421,005 B2 | 4/2013 | Musselman | |
| 8,592,756 B2 * | 11/2013 | Ouyang | H01J 49/0404 250/281 |
| 8,686,351 B2 * | 4/2014 | Ouyang | H01J 49/0404 250/281 |
| 8,803,085 B2 * | 8/2014 | Ouyang | H01J 49/0404 250/281 |
| 8,963,079 B2 * | 2/2015 | Ouyang | H01J 49/0404 250/281 |
| 2001/0054685 A1 * | 12/2001 | Franzen | H01J 49/40 250/287 |
| 2004/0169137 A1 | 9/2004 | Westphall et al. | |
| 2004/0217280 A1 | 11/2004 | Schneider et al. | |
| 2005/0236374 A1 | 10/2005 | Blankenship | |
| 2005/0253063 A1 | 11/2005 | Tan et al. | |
| 2005/0258353 A1 * | 11/2005 | Berkout | H01J 49/0045 250/281 |
| 2006/0054805 A1 | 3/2006 | Flanagan et al. | |
| 2007/0114384 A1 * | 5/2007 | Berkout | H01J 49/0045 250/287 |
| 2008/0067359 A1 | 3/2008 | Musselman | |
| 2008/0087812 A1 * | 4/2008 | Musselman | H01J 49/0404 250/285 |
| 2008/0156985 A1 * | 7/2008 | Venter | H01J 49/165 250/288 |
| 2008/0164409 A1 * | 7/2008 | Schultz | G01N 27/622 250/282 |
| 2009/0321655 A1 | 12/2009 | Makarov et al. | |
| 2010/0038533 A1 | 2/2010 | Makarov et al. | |
| 2010/0044560 A1 * | 2/2010 | Basile | G01N 33/6803 250/282 |
| 2010/0059674 A1 * | 3/2010 | Chen | H01J 49/145 250/288 |
| 2010/0078550 A1 * | 4/2010 | Wiseman | G01N 1/405 250/282 |
| 2011/0240844 A1 | 10/2011 | Ouyang et al. | |
| 2012/0305758 A1 * | 12/2012 | Park | H01J 49/063 250/282 |
| 2012/0305759 A1 * | 12/2012 | Park | H01J 49/421 250/282 |
| 2012/0312980 A1 * | 12/2012 | Whitehouse | H01J 49/0413 250/282 |
| 2013/0009051 A1 * | 1/2013 | Park | H01J 49/063 250/282 |

OTHER PUBLICATIONS

International Preliminary Report on Patentablility for PCT/US2009/059514, issued Apr. 19, 2011.
International Search Report for PCT/US2009/059524, mailed May 24, 2010.
Takats, Z 'Ambient MS using desorption electrospray ionization.' JMass. Spectrom., 2005, 40:1261-1275.
Written Opinion of the International Searching Authority for PCT/US2009/059514, completed Feb. 23, 2010.

* cited by examiner

SYSTEMS AND METHODS FOR TRANSFER OF IONS FOR ANALYSIS

RELATED APPLICATION

The present application is a continuation of U.S. nonprovisional application Ser. No. 14/594,217, filed Jan. 12, 2015, which is a continuation of U.S. nonprovisional application Ser. No. 14/454,811, filed Aug. 8, 2014, which is a continuation of U.S. nonprovisional application Ser. No. 14/180,915, filed Feb. 14, 2014, which is a continuation of U.S. nonprovisional application Ser. No. 13/937,913, filed Jul. 9, 2013, which is a continuation of U.S. nonprovisional application Ser. No. 13/727,840 filed Dec. 27, 2012, which is a continuation of U.S. nonprovisional application Ser. No. 13/122,651, filed Jun. 20, 2011, which is a 371 national phase application and claims the benefitof and priority to PCT/US09/59514, filed Oct. 5, 2009, which PCT application claims the benefit of and priority to U.S. provisional patent application Ser. No. 61/104,793, filed Oct. 13, 2008, the content of each of which is incorporated herein by reference in its entirety.

GOVERNMENT SUPPORT

This invention was made with government support under 2007-ST-069-TSL001 awarded by Department of Homeland Security and N000140510454 awarded by U.S. Navy Office of Naval Research. The government has certain rights in the invention.

TECHNICAL FIELD

The invention generally relates to systems and methods for transfer of ions for analysis.

BACKGROUND

In the field of analytical chemistry, the demand for direct sampling under ambient conditions has increased, and this has led to the development of a variety of ambient ionization sources. Ambient ionization sources ionize analytes in the ambient environment (in situ) with no intrinsic requirement for sample preparation. This advantage allows for real-time, on-site detection, saving time and resources.

A typical set-up that uses an ambient ionization source to analyze ions from a sample is configured such that the ionization source is uncoupled from a mass analyzer, such as a mass spectrometer (MS). The mass spectrometer must be located sufficiently close to the ionization source (on the order of about 2 cm or less) so that the ions that are generated will transfer to an inlet of the mass spectrometer. The opening of the MS inlet is typically smaller than 700 μm, due to the fact that a vacuum must be maintained inside a manifold where ions are mass analyzed. In applications in which the ions are generated far from the MS inlet (on the order of about 5 cm), it is difficult, if not impossible, to transfer the ions to the mass analyzer. Thus the distance between the ambient ionization source and the mass analyzer limits the use of these ambient ionization sources.

Further, the ions generated from an ionization source at atmospheric pressure, such as an electrospray ionization (ESI) or desorption electrospray ionization (DESI), also have a wide angular dispersion. The intake of the ions by the MS inlet of a small opening is relatively inefficient. In an application in which analytes over a large area need to be analyzed or monitored simultaneously, it is highly desirable that the ions generated be transferred into the MS inlet at high efficiency.

There is a need for devices that can facilitate transfer of ions from an ambient ionization source to an inlet of a mass spectrometer.

SUMMARY

The invention provides systems that use a gas flow to bring ions into a confined space and generate a laminar gas flow that focuses the ions and facilitates transfer of the ions from an ambient ionization source to an inlet of an ion analysis device, such as a mass spectrometer. Systems of the invention allow for transfer of ions over long distances (e.g., at least about 5 cm), and also allow for sampling over large areas (e.g., at least about areas of 4 cm×3 cm or 10 cm×10 cm). For example, systems of the invention allow for use of ambient ionization sources under conditions in which the ionization source cannot be positioned sufficiently close to an inlet of an ion analysis device for collection of ions generated from a sample.

An aspect of the invention provides a system for analyzing a sample including an ionizing source for converting molecules of a sample into gas phase ions in a region at about atmospheric pressure, an ion analysis device, and an ion transfer member operably coupled to a gas flow generating device, in which the gas glow generating device produces a laminar gas flow that transfers the gas phase ions through the ion transfer member to an inlet of the ion detection device.

A typical prior art set-up that uses an ambient ionization source positions the ionization source about 2 cm or closer to the inlet of the ion analysis device. Distances greater than 2 cm between the ionization source and the inlet of the ion analysis device result in diffusion of ions into the atmosphere and degradation of signal, i.e., inefficient or no transfer of ions to the ion analysis device. Systems and methods of the invention generate a laminar gas flow, thus allowing for efficient transfer of ions over long distances without significant loss of signal intensity, such as distances of at least about 5 cm, at least about 10 cm, at least about 20 cm, at least about 50 cm, at least about 100 cm, at least about 500 cm, at least about 1 m, at least about 3 m, at least about 5 m, at least about 10 m, and other distances.

In certain embodiments, the ion analysis device is a mass spectrometer. In other embodiments, the ion analysis device is an ion mobility spectrometer. In other embodiments, the ion analysis device is a simple ion detector such as a Faraday cup. In certain embodiments, the ions are detected or analyzed after transfer. In other embodiment, the ions are re-collected after transfer.

In certain embodiments, the gas flow generating device is a pump having a high flow rate and a low compression ratio, such as a house vacuum, that is connected to the ion transfer member to produce a laminar gas flow for transfer of ions to the inlet of the ion analysis device. In other embodiments, the gas flow generating device is the ambient ionization source. For example, a source used for desorption electrospray ionization (DESI) generates a gas flow sufficient to produce a laminar flow through the ion transfer member, and thus produces a laminar gas flow that transfers the gas phase ions to an inlet of the ion analysis device. In other embodiments, the gas flow generating device is a combination of the pump and the gas jet of the ambient ionization source.

The system may further include an electric focusing lens device operably coupled to the ion transfer member to facilitate transfer of ions to the inlet of the ion analysis device. The system may further include an air dynamic lens device operably coupled to the ion transfer member to facilitate focusing of heavy ions to the inlet of the ion analysis device. The system may further include an electro-hydrodynamic lens device operably coupled to the ion transfer member. The system may further include at least one vacuum pump connected to the ion detection device. The system may further include a computer operably connected to the system. The system may further include a stage for holding the sample.

In certain embodiments, the ion transfer member is coupled with a dielectric barrier discharge to enhance ion transfer efficiency. In other embodiments, a distal end of the ion transfer member includes a plurality of inlets for transferring ions from multiple locations to the inlet of the ion analysis device.

The ion transfer member may be any connector that allows for production of a laminar flow within it and facilitates transfer of ions without significant loss of ion current. An exemplary ion transfer member is a tube. The tube may be composed of rigid material, such as metal or glass, or may be composed of flexible material such as TYGON tubing. The ion transfer member may be any shape as long the shape allows for production of a laminar flow within it and facilitates transfer of ions without significant loss of ion current. For example, the ion transfer member may have the shape of a straight line. Alternatively, the ion transfer member may be curved or have multiple curves.

The ionizing source may operate by any technique that is capable of converting molecules of a sample into gas phase ions at substantially atmospheric pressure, i.e., an atmospheric pressure ionization source or an ambient ionization source. Exemplary techniques include electrospray ionization, nano-electrospray ionization, atmospheric pressure matrix-assisted laser desorption ionization, atmospheric pressure chemical ionization, desorption electrospray ionization, atmospheric pressure dielectric barrier discharge ionization, atmospheric pressure low temperature plasma desorption ionization, and electrospray-assisted laser desorption ionization.

The ions generated from the ionization source are sent through the ion transfer member and are transferred to an inlet of an ion analysis device. Exemplary ion analysis devices include a mass spectrometer, and an ion mobility spectrometer. Exemplary mass spectrometers include an ion trap, a quadrupole filter, a time of flight, a sector, an ion cyclotron resonance trap, and an orbitrap mass spectrometer.

Systems of the invention may analyze samples in any state, e.g., solid phase, liquid phase, or gas phase. The sample may be of any origin, such as a biological origin or a non-biological origin. Exemplary samples include an industrial work piece, a pharmaceutical product or ingredient, a food or food ingredient, a toxin, a drug, an explosive, a bacterium, or a biological tissue or fluid.

Another aspect of the invention provides a method of analyzing a sample including ionizing a sample to convert molecules of the sample into gas phase ions in a region at about atmospheric pressure, providing an ion transfer member coupled to a gas flow generating device to produce a laminar gas flow that transfers the gas phase ions to an inlet of the ion analysis device, and analyzing the ions.

BRIEF DESCRIPTION OF THE DRAWINGS

FIG. 23A shows an MS spectrum of 300 ng/mL melamine in water/methanol (v:v=1:1), loading volume 3 µL (absolute melamine amount of 0.9 ng). FIG. 23B shows an MS spectrum of 5 µg/mL melamine in whole milk, loading volume 3 µL (absolute melamine amount of 15 ng). FIG. 23C shows an MS spectrum of 5 µg/g melamine in milk powder, loading volume 5 mg (absolute melamine amount of 25 ng). FIG. 23D shows an MS spectrum of 1 µg/mL melamine in synthetic urine, loading volume 3 µL (absolute melamine amount of 3 ng). Inserts: MS/MS product ion spectrum of the protonated molecule.

DETAILED DESCRIPTION

Figure 1:
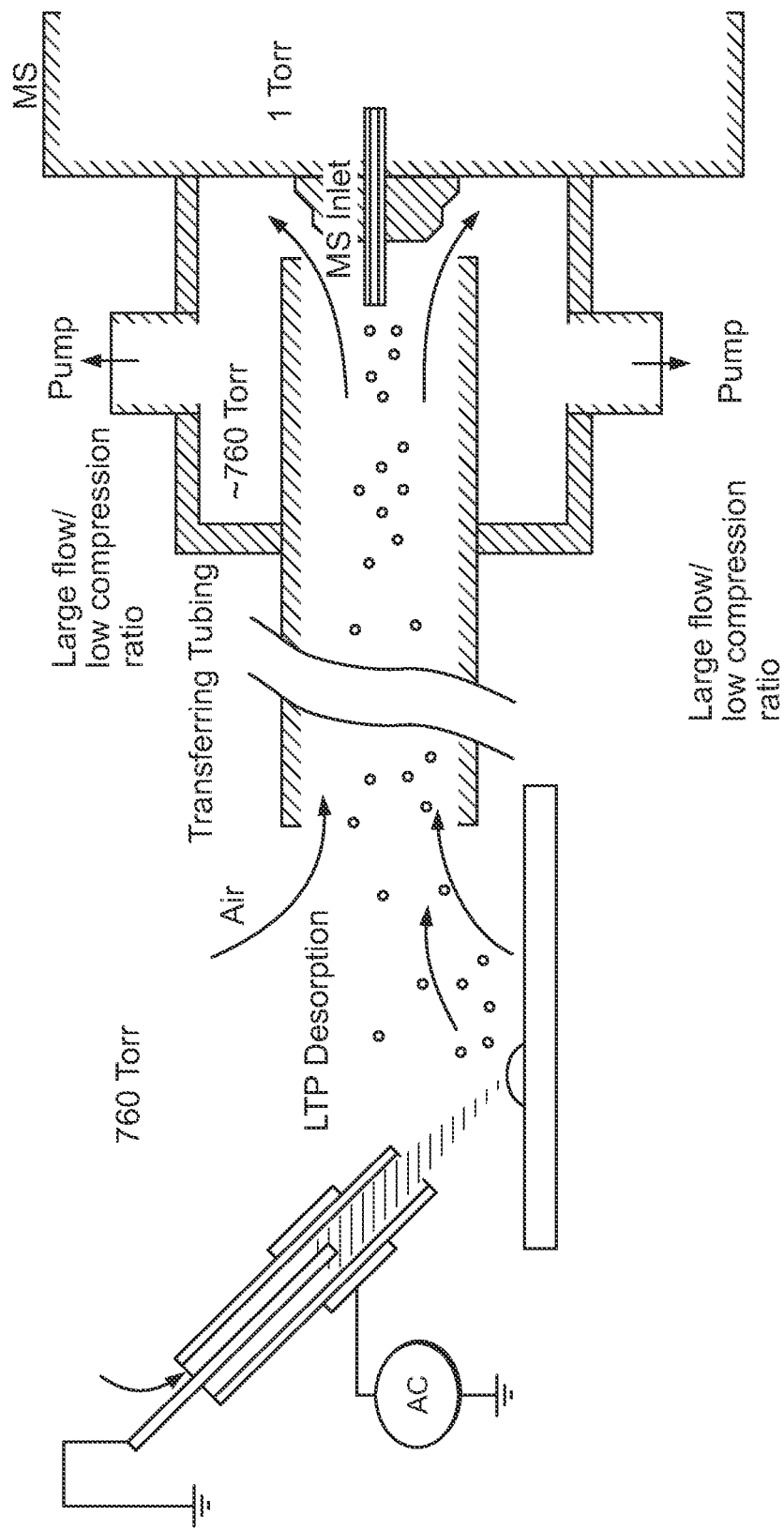
FIG. 1 is a schematic showing an embodiment of a system for transferring ions from an ambient ionization source to an inlet of an ion analysis device.

A typical prior art set-up that uses an ambient ionization source positions the ionization source about 2 cm or closer to the inlet of the ion analysis device. The transfer of the ion into the inlet of a mass spectrometer relies on the gas flow into the inlet under the influence of the vacuum of the spectrometer and the electric field in the surrounding area. The gas flow is typically low due to the low conductance of the inlet, which serve as the conductance barrier between atmosphere and vacuum manifold. Distances greater than 2 cm between the ionization source and the inlet of the ion analysis device result in diffusion of ions into the atmosphere and degradation of signal, i.e., inefficient or no transfer of ions into the ion analysis device. Systems and methods of the invention generate a laminar gas flow that allows for efficient transfer of ions without significant loss of signal intensity over longer distances, such as distances of at least about 5 cm, at least about 10 cm, at least about 20 cm, at least about 50 cm, at least about 100 cm, at least about 500 cm, at least about 1 m, at least about 3 m, at least about 5 m, at least about 10 m, and other distances.

Systems and methods of the invention are useful for chemical analysis in situations in which it is important for the instrument and the object being examined to be in different locations. For example, systems and methods herein are useful for screenings at security checkpoints, e.g., airport security checkpoints or road-side checkpoints, for interrogation of luggage surfaces for the detection of foreign substances.

An aspect of the invention provides a system for analyzing a sample including an ionizing source for converting molecules of a sample into gas phase ions in a region at about atmospheric pressure, an ion analysis device, and an ion transfer member operably coupled to a gas flow generating device, in which the gas flow generating device produces a laminar gas flow that transfers the gas phase ions to an inlet of the ion analysis device.

Systems of the invention provide enlarged flow to carry ions from a distant sample to an inlet of an ion analysis device, such as an inlet of a mass spectrometer. The basic principle used in the transport device is the use of the gas flow to direct gas and ions into the ion transfer member and to form a laminar flow inside the ion transfer member to keep the ions away from the walls while transferring the gas and ions through the ion transfer member. The analyte ions of interest are sampled at some point downstream along the ion transfer member. The laminar flow is achieved by balancing the incoming and outgoing gas flow. Thus recirculation regions and/or turbulence are avoided. Thus, the generated laminar flow allows for high efficient ion transport over long distance or for sampling of ions over large areas.

Systems of the invention also provide enlarged flow to carry ions from the ion source to an inlet of a miniature mass spectrometer, which has small pumping systems and compromised gas intake capability at the inlet. Additional gas flow provided by a miniature sample pump connected with the ion transfer member facilitates ion transfer from an ambient ionization source to the vicinity of the inlet of the miniature mass spectrometer. Thus the intensity of the ions for the analytes of interest is increased for mass analysis.

As shown in FIG. 1, an ion transfer member, e.g., a tube with an inner diameter of about 10 mm or greater, is used to transfer ions from the ionization source to the inlet of an ion analysis device, e.g., a mass spectrometer. The larger opening of the ion transfer member, as compared to the opening of the inlet of the ion analysis device, is helpful for collection of sample ions generated in a large space, e.g. on a surface of large area. The large flow conductance of the ion transfer member allows the gas carrying ions to move toward the inlet of the ion analysis device at a fast flow rate. The ion transfer member is coupled to a gas flow generating device. The gas flow generating device produces a gas flow inside the ion transfer member. The inlet of the ion analysis device receives the ions transferred from the ambient ionization source.

The ion transfer member may be any connector that allows for production of a laminar flow within it and facilitates transfer of ions without significant loss of ion current. Exemplary ion transfer members include tubes, capillaries, covered channels, open channels, and others. In a particular embodiment, the ion transfer member is a tube. The ion transfer member may be composed of rigid material, such as metal or glass, or may be composed of flexible material such as plastics, rubbers, or polymers. An exemplary flexible material is TYGON tubing.

The ion transfer member may be any shape as long the shape allows for the production of a flow to prevent the ions from reaching the internal surfaces of the ion transfer member where they might become neutral. For example, the ion transfer member may have the shape of a straight line. Alternatively, the ion transfer member may be curved or have multiple curves.

The ion transfer member is coupled to a gas flow generating device. The gas flow generating device is such a device capable of generating a gas flow through the ion transfer member. The gas flow generating device facilitates transfer of the ions from the ambient ionization source to the inlet of the ion analysis device. In certain embodiments, the gas flow generating device is a pump with a high flow rate and a low compression ratio. An example of such a pump is that found in a shop vacuum or a small sample pump. The proper pumps used for the coupling are different from those used for a mass spectrometer, e.g. a rotary vane pump or a turbo molecular pump, which pumps have a high compression ratio. The high compression ratio pumps of a mass spectrometer cannot be connected to the atmosphere through an opening of the conductance described here. For example, Cotte-Rodríguez et al. (Chem. Commun., 2006, 2968-2970) describe a set-up in which the inlet of the mass spectrometer was elongated and gas flow generated by the pump inside a mass spectrometer was used to transfer ions over a distance up to 1 m. The ions were transferred from the atmosphere to a region at about 1 torr. A significant loss in signal occurred for the transfer of the ions using the set-up described in Cotte-Rodríguez, and ions generated over a large area could not be efficiently collected into the inlet.

In other embodiments, the gas flow generating device is the ambient ionization source. For example, a source used for desorption electrospray ionization (DESI) generates a gas flow sufficient to produce a laminar flow through the ion transfer member, and thus produces a laminar gas flow that transfers the gas phase ions over a long distance to an inlet of the ion analysis device.

Figure 9:
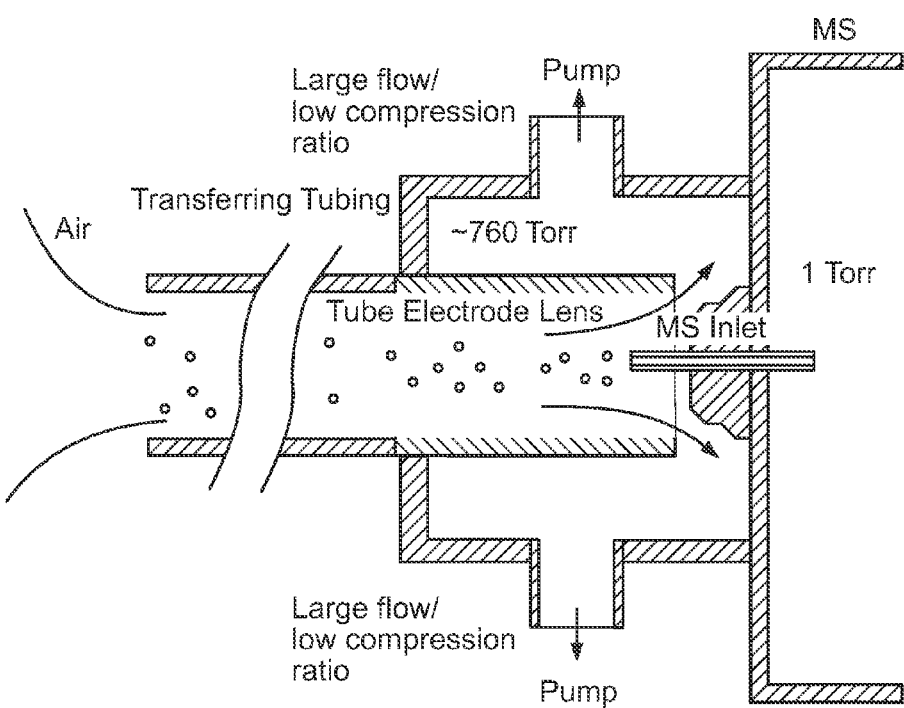
FIG. 9 is a schematic showing a tube electric lens that can be implemented to focus the charged particles toward the center of the transfer tubing.
Figure 10:
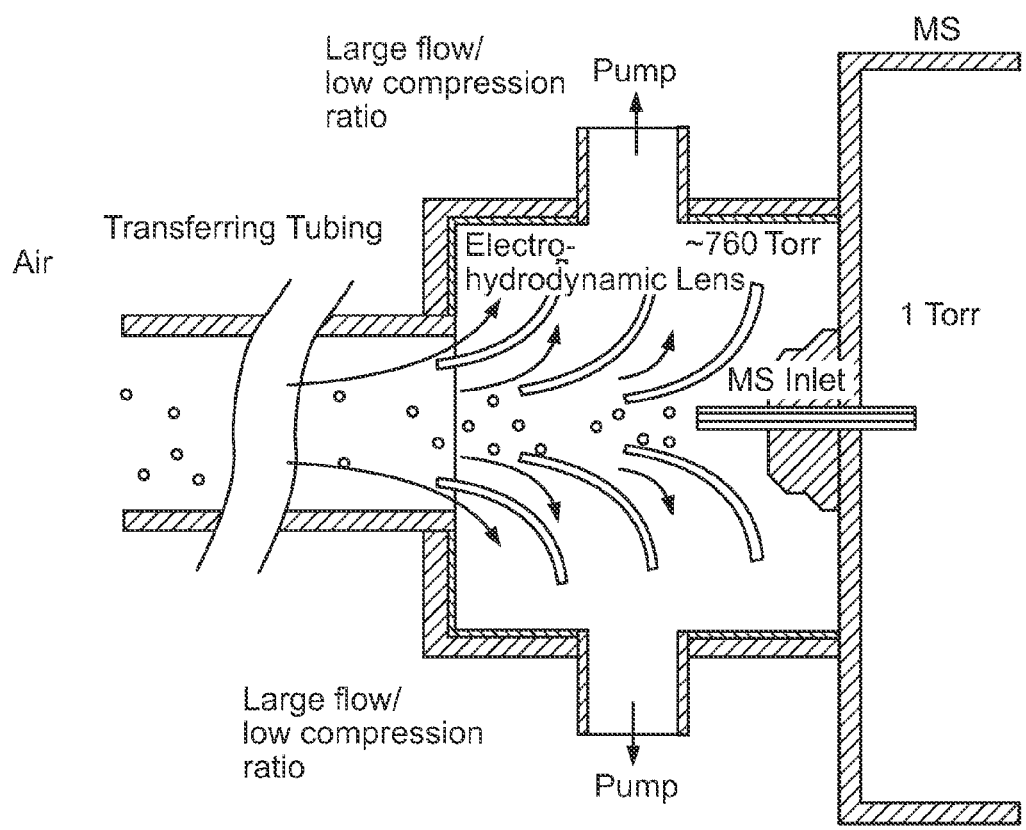
FIG. 10 is a schematic showing an electro-air dynamic lens system that can be implemented to use the air dynamic effects to focus the heavier particles and to use the electric field to focus the charged particles toward the center.

Numerous additional devices may be coupled with the ion transfer member to further facilitate transfer of the ions from the ambient ionization source to the inlet of the ion analysis device. For example, an electric lens may be used to focus the ions toward the center of the ion transfer member while the gas flow generating device pumps away neutral gases (See FIG. 9). In other embodiments, an electro-hydrodynamic lens system may be implemented to use the air dynamic effects to focus the heavier particles and to use the electric field to focus the charged particles toward the center of the ion transfer member (See FIG. 10).

Figure 8:
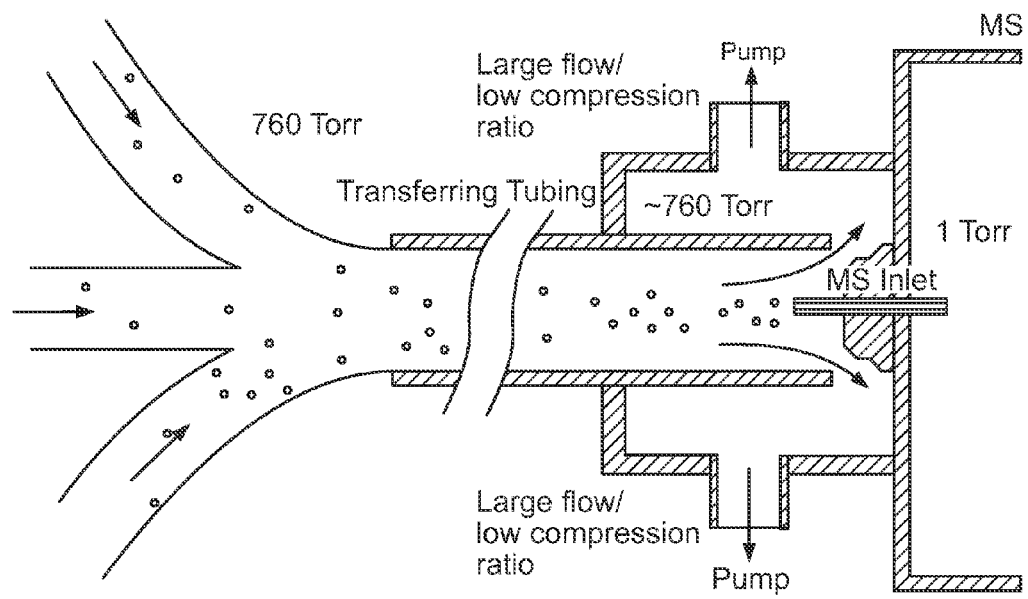
FIG. 8 is a schematic showing that ions generated from samples at multiple locations can be transferred to mass spectrometer for analysis, simultaneously or in a sequence.

In other embodiments, a distal end of the ion transfer member may include a plurality of inlets for transferring ions from multiple locations to the inlet of the ion analysis device. FIG. 8 is a schematic showing that ions generated from samples at multiple locations can be transferred to a mass spectrometer for analysis, in a simultaneous or sequential fashion.

Figure 11A:
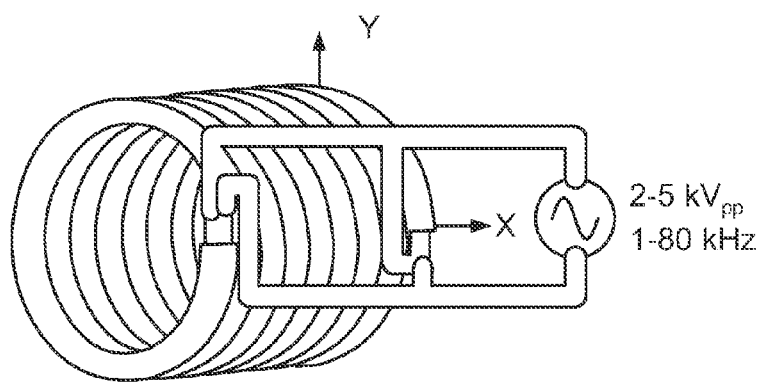
FIG. 11A is a schematic of a dielectric barrier discharge (DBD) tubing.
Figure 11B:
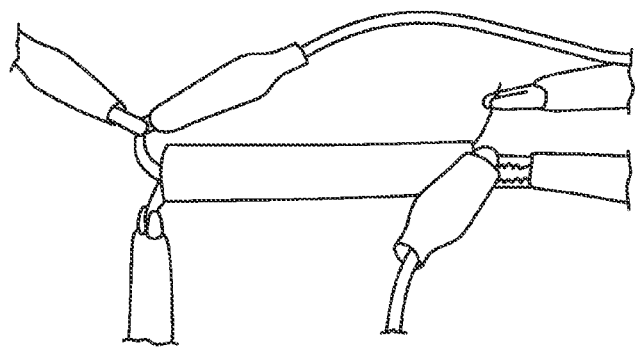
FIG. 11B is a photograph showing DBD tubing made with double strand speaker wire.
Figure 11C:
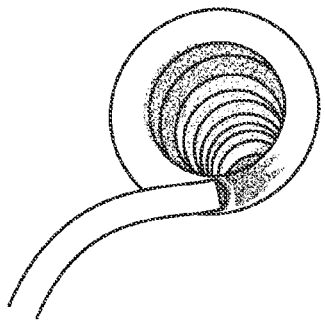
FIG. 11C is a photograph showing the DBD inside the tubing with high voltage AC applied.

In still other embodiments, the ion transfer member includes additional features to prevent ions from being adsorbed onto the inside wall. As shown in FIG. 11, a dielectric barrier discharge (DBD) tubing is made from a double stranded speaker wire. The insulator of the wire serves as the dielectric barrier and the DBD occurs when high voltage AC is applied between the two strands of the wire. The DBD inside the tube prevents the ions from adsorbing onto the wall and provide a charge-enriched environment to keep the ions in the gas phase. This DBD tube can also be used for ionizing the gas samples while transferring the ions generated to the inlet of the ion analysis device. The DBD tube can also be used for ion reactions while transferring the ions generated to the inlet of the ion analysis device.

Prior to entering the ion transfer member, ions of the sample are ionized using an ambient ionization source or an atmospheric pressure ionization source. Exemplary ambient ionization techniques include electrospray ionization (Fenn, J. B.; Mann, M.; Meng, C. K.; Wong, S. F.; Whitehouse, C. M. Science 1989, 246, 64-71; Yamashita, M.; Fenn, J. B. J. Phys. Chem. 1984, 88, 4451-4459), nano-electrospray ionization (Karas et al., Fresenius J Anal Chem, 366:669-676, 2000), atmospheric pressure matrix-assisted laser desorption ionization (Laiko, V. V.; Baldwin, M. A.; Burlingame, A. L. Anal. Chem. 2000, 72, 652-657; and Tanaka, K.; Waki, H.; Ido, Y.; Akita, S.; Yoshida, Y.; Yoshida, T.; Matsuo, T. Rapid Commun. Mass Spectrom. 1988, 2, 151-153), atmospheric pressure chemical ionization (Carroll, D. L; Dzidic, L; Stillwell, R. N.; Haegele, K. D.; Horning, E. C. Anal. Chem. 1975, 47, 2369-2373), desorption electrospray ionization (Takats et al., U.S. Pat. No. 7,335,897; and Takats, Z.; Wiseman, J. M.; Gologan, B.; Cooks, R. G. Science 2004, 306, 471-473), atmospheric pressure dielectric barrier discharge ionization (Shiea, J.; Huang, M. Z.; Hsu, H. J.; Lee, C. Y.; Yuan, C. H.; Beech, L; Sunner, J. Rapid Commun. Mass Spectrom. 2005, 19, 3701-3704), atmospheric pressure low temperature plasma desorption ionization (Ouyang et al. International patent publication WO 2009/102766), and electrospray-assisted laser desorption ionization (Shiea, J.; Huang, M. Z.; Hsu, H. J.; Lee, C. Y.; Yuan, C. H.; Beech, L; Sunner, J. Rapid Commun. Mass Spectrom. 2005, 19, 3701-3704). The ions of the sample then move through the ion transfer member.

After moving through the ion transfer member, the ions are then separated based on their mass/charge ratio or their mobility or both their mass/charge ratio and mobility. For example, the ions can be accumulated in an ion analysis device such as a quadrupole ion trap (Paul trap), a cylindrical ion trap (Wells, J. M.; Badman, E. R.; Cooks, R. G., Anal. Chem., 1998, 70, 438-444), a linear ion trap (Schwartz, J. C.; Senko, M. W.; Syka, J. E. P., J. Am. Soc. Mass Spectrom, 2002, 13, 659-669), an ion cyclotron resonance (ICR) trap, an orbitrap (Hu et al., J. Mass. Spectrom., 40:430-433, 2005), a sector, or a time of flight mass spectrometer. Additional separation might be based on mobility using ion drift devices or the two processes can be integrated.

Systems of the invention can analyze samples in any state, e.g., solid phase, liquid phase, or gas phase. The sample may be of any origin, such as a biological origin or a non-biological origin. Exemplary samples include an industrial work piece, a pharmaceutical product or ingredient, a food or food ingredient, a toxin, a drug, an explosive, a bacterium, or a biological tissue or fluid.

A sample can be from a mammal, e.g. a human tissue or body fluid. A tissue is a mass of connected cells and/or extracellular matrix material, e.g. skin tissue, nasal passage tissue, CNS tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, phlegm, saliva, sweat, amniotic fluid, mammary fluid, and cerebrospinal fluid (CSF), such as lumbar or ventricular CSF. A sample may also be a fine needle aspirate or biopsied tissue. A sample also may be media containing cells or biological material.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

EXAMPLES

Example 1

Long Distance Ion Transfer

Figure 2:
FIG. 2 is a photograph showing a setup for long distance ion transfer.

A Thermo Scientific LTQ was modified to allow long distance ion transfer via assisted vacuum from an external low temperature plasma (LTP) source. The modified Ion Max source (ion source for LTQ mass spectrometer, ThermoFisher, San Jose, Calif.) was used to guide the ions from long distances into the inlet of the LTQ mass spectrometer. A common shop vacuum was used as a vacuum device to provide the assisted flow to carry the ions over long distances. The setup used is shown in FIG. 2. An adjustable inlet tube that bridges the ion transfer tube to the MS inlet allowed for optimization of the ion signal. Both rigid tubing (metal conduit, and glass) as well as flexible (tygon tubing) were used in this example, all showing long distance ion transfer abilities.

Figure 3:
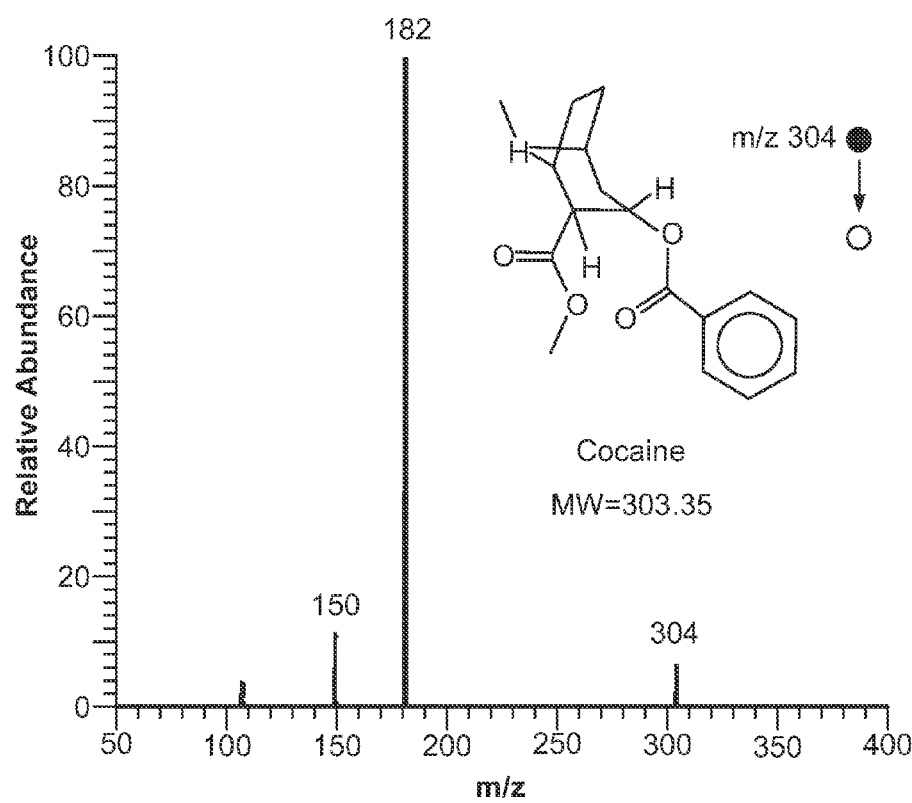
FIG. 3 is a tandem mass spectrum of 1.7 μg cocaine on glass desorbed/ionized via LTP helium and transferred 4 ft using a flexible TYGON tubing.
Figure 4:
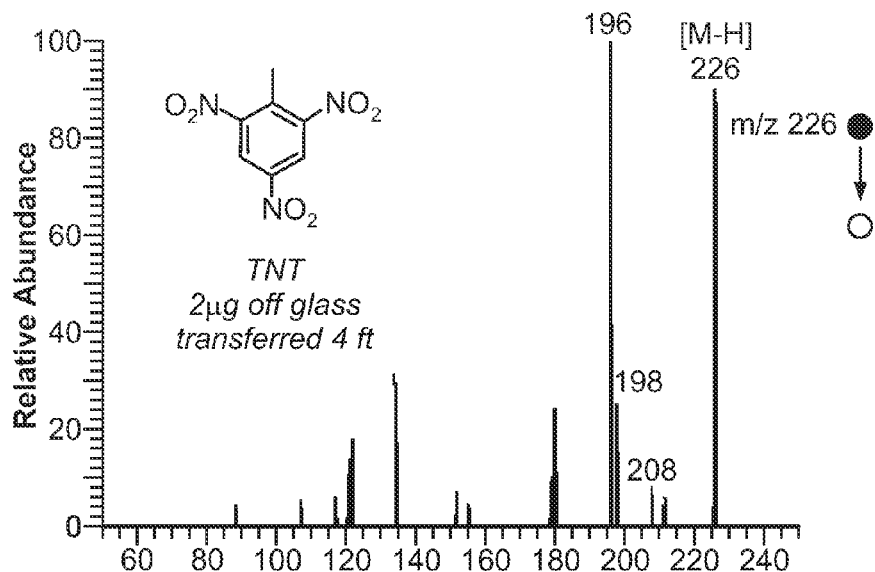
FIG. 4 is a tandem mass spectrum of 2 μg of TNT on glass desorbed/ionized via LTP helium and transferred 4 ft using a flexible TYGON tubing.

The LTP probe was utilized as a desorption ionization source with helium as the discharge gas. This setup was initially used for ion transfer of drugs and explosives. 1.7 µg of cocaine and 2 µg of TNT were spotted onto separate glass slides and the slides were placed on a stage 4 ft from the inlet of the mass spectrometer. 4 ft of Tygon tubing was used as the ion transfer member to transfer ions from the LTP probe to the inlet of the mass spectrometer. Data herein show successful detection of the cocaine in the positive MS/MS mode, as shown in FIG. 3. Data herein also show successful detection of the TNT in the negative MS/MS mode, as shown in FIG. 4.

Figure 5:
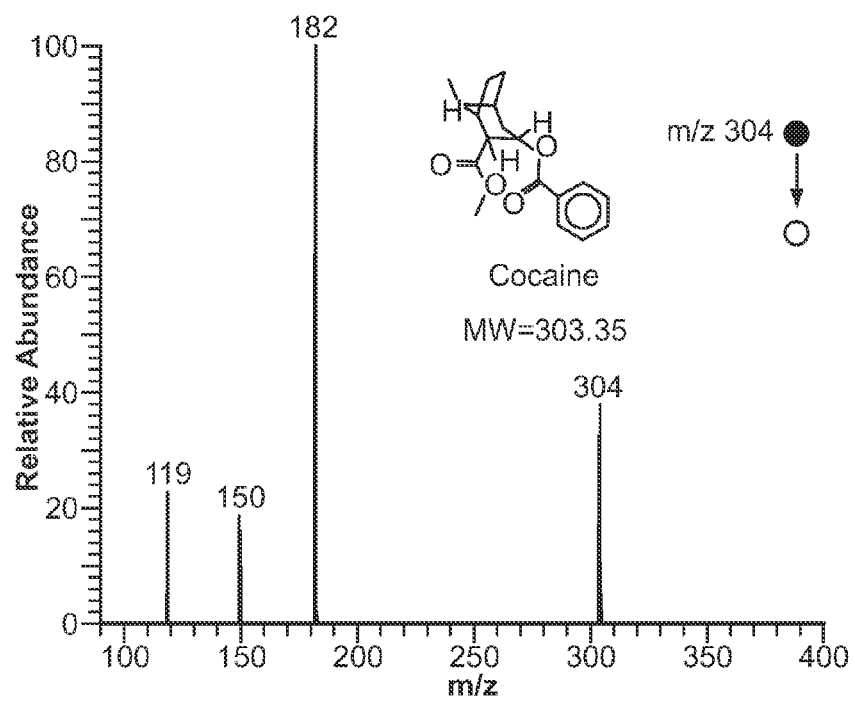
FIG. 5 is a tandem mass spectrum of 1.7 μg cocaine on glass desorbed/ionized via LTP helium and transferred 10 ft in stainless steel ¾" diameter conduit.

The cocaine sample was then used over several hours for tests with 10 ft of metal conduit (FIG. 5), 15 ft of Tygon tubing, and also 30 ft of Tygon tubing, all resulting in positive confirmation of cocaine in the positive MS/MS mode. It was also observed that the tubing did not have to be straight, i.e., curved tubing still successfully transferred the ions to the inlet of the mass spectrometer.

Example 2

Large Area and Long Distance Ion Transfer

Figure 6:
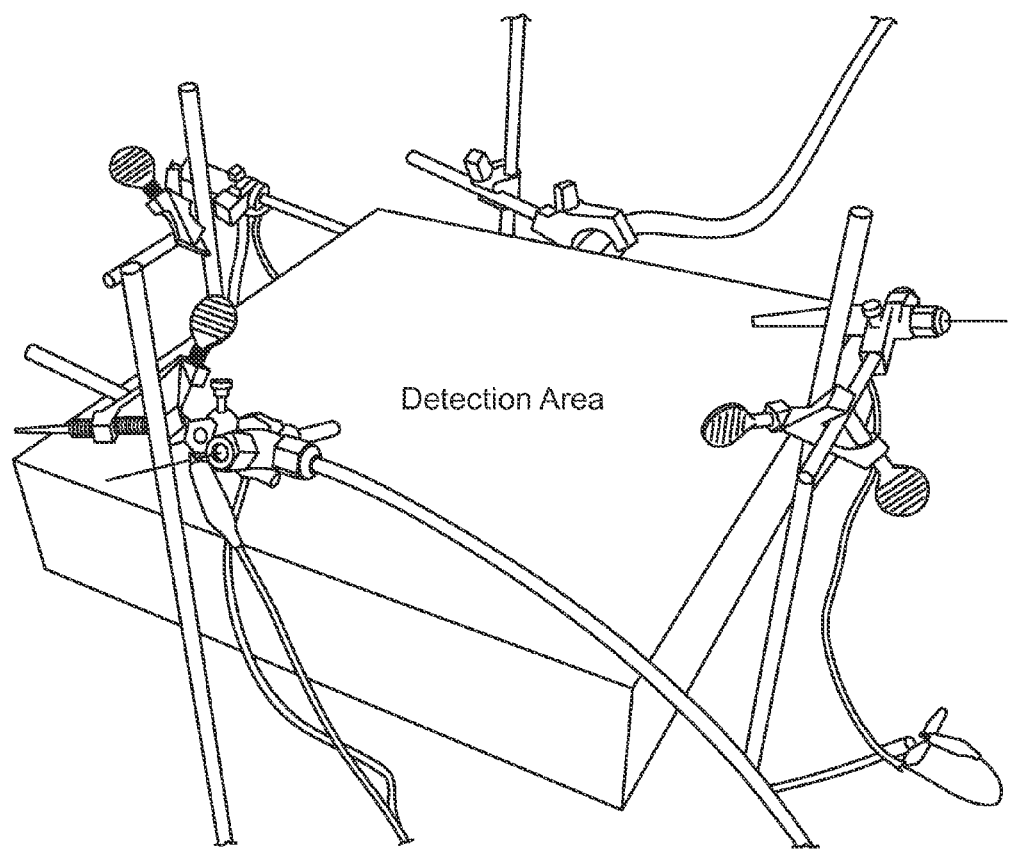
FIG. 6 is a photograph showing a setup for long distance ion transfer using large area analysis via LTP probes.

Utilizing the apparatus shown in FIG. 2, large area analysis was done by using three LTP probes to sample a large area. FIG. 6 shows the setup of the three LTP probes utilizing 4 ft (1.2 m) of Tygon tube for long distance transfer. 1.7 µg of cocaine and 1 µg of atrazine were spotted onto a glass slide and analyzed via the LTP probe setup. The elliptical shape outlined in black marker on the cardboard box is the approximate area of detection for both 1.7 µg of cocaine and 1 µg of atrazine utilizing the long distance transfer apparatus, which is >>100 cm². Positive mode tandem mass spectrometry was used to confirm the molecules transfer over the 4 ft distance.

Figure 7A:
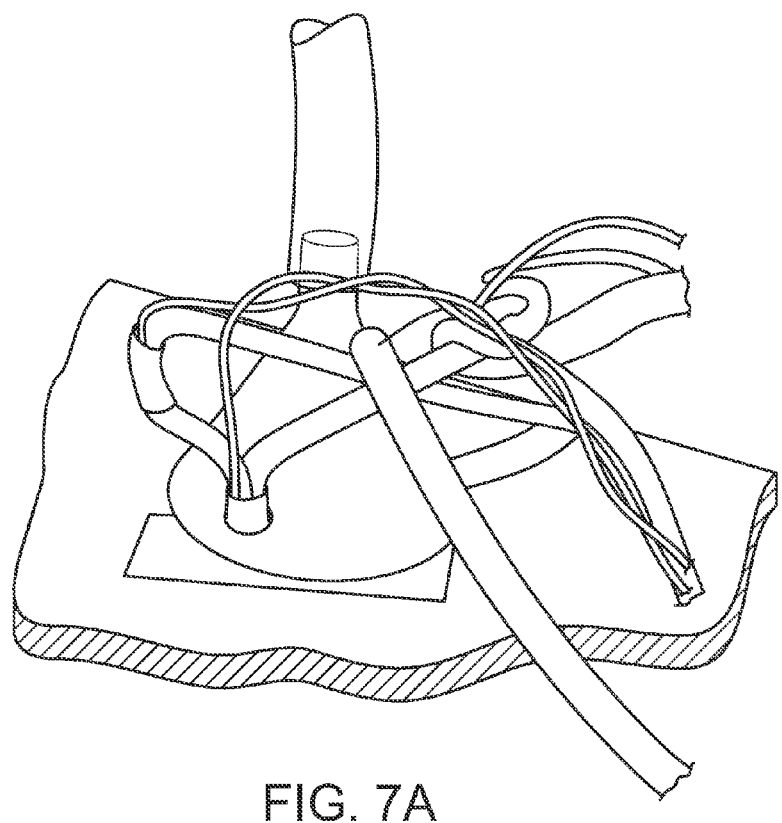
FIG. 7A is a photograph showing an LTP large area sampling funnel (area=33 cm$^2$) with four LTP probes coupled with long distance ion transfer instrumentation.
Figure 7B:
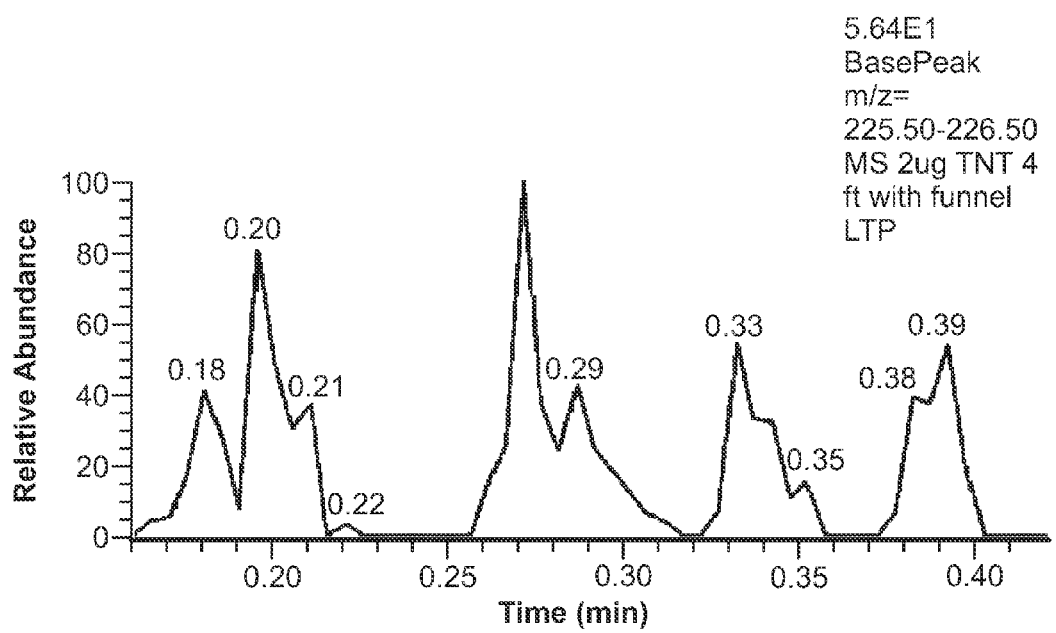
FIG. 7B is a total ion chronogram of m/z 226 transferred 4 ft, showing when funnel is over 2 μg of TNT on glass slide.

An LTP large area funnel was coupled to the apparatus shown in FIG. 2 via the 4 foot tygon tubing. Utilizing helium as the discharge gas, 2 µg of TNT on a glass slide were analyzed, shown in the top of FIG. 7. The bottom of FIG. 7 shows the total ion current (TIC) of m/z 226 (deprotonated TNT) transferred through 4 ft of Tygon tubing, clearly showing the detection of TNT when the funnel was placed over the sample. When the funnel was removed away from the sample the TIC was close to zero. A distance of >1" could be maintained between the surface and glass slide and successful detection could occur while the area of detection was limited by the funnel area (33 cm²).

Example 3

Ion Transport with Desorption Electrospray Ionization (DESI)

Figure 12:
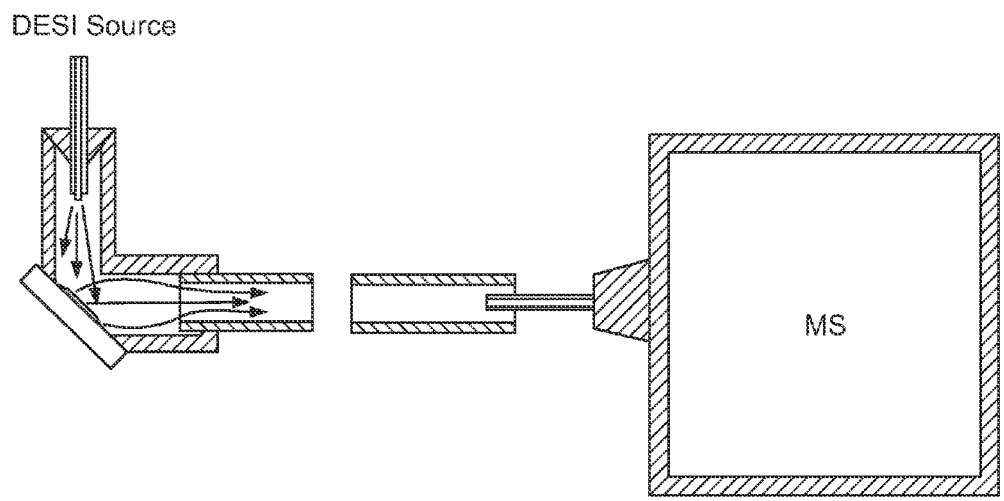
FIG. 12 is a schematic showing a desorption electrospray ionization (DESI) long distance transport setup.

The transport of ionic species in DESI sources was achieved over a long distance (at least 1 m) by using a similar system as described in the Example above. However, the system was modified to remove the pump and use the DESI sources as the gas flow generating device due to the high flow rate of gas generated from the DESI source. The ejecting gas from a DESI source, after impact with the desorption surface, was allowed to pass through a long 0.25" metal tube. The MS capillary was used to sample the ions at some suitable distance downstream of the gas flow. The schematic of this setup is shown ion FIG. 12. In comparison with a previously reported development using a pressure tight enclosure (Venter, A.; Cooks, R. G. Anal. Chem., 2007, 79 (16), pp 6398-6403; United States Patent Application 2008/0156985), a large opening at the distal end allows the DESI gas flow to exit to allow the formation of a laminar flow and to avoid the recirculation and turbulence inside the ion transfer member.

Example 4

Long Distance Ion Transfer—DESI

In a set-up in which the gas flow generating device was the DESI source, the gas jet ejected from the DESI source itself was used for ion transport, i.e., long distance ion transport was achieved by using an ion transport member without a pump. The gas jet emanating from DESI source was used to transport ions.

Figure 13:
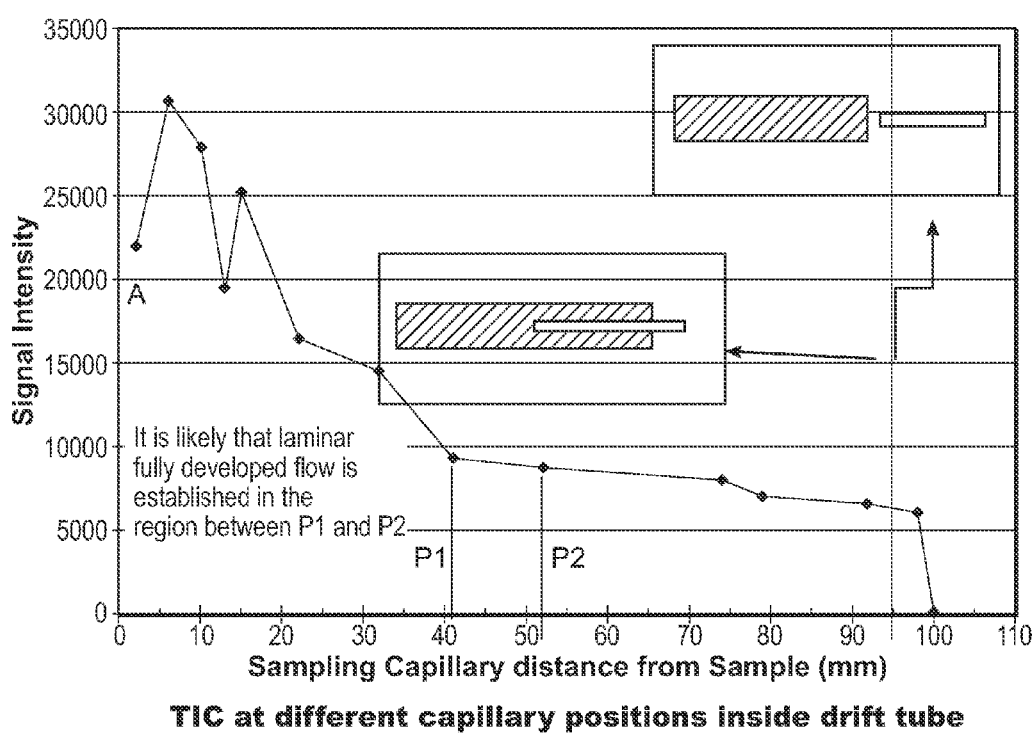
FIG. 13 is a graph showing variation of TIC with sampling distance. A rhodamine ink spot was used as analyte. It was observed that signal fall rate decreases beyond 40 mm. A fully developed laminar flow could be generated between 40 mm and 50 mm downstream in the drift tube.

Rhodamine ink was used as the analyte. A red ink spot was made on a glass slide using Sharpie ink, and the TIC during analysis was plotted against signal intensity (FIG. 13). Initially, the capillary was close to the desorption surface (a few millimeters). As the distance between the sample surface and the MS inlet was increased, the signal drop rate was initially high, and the drop rate eventually slowed and then reached a stable level at which an approximately constant signal intensity was obtained irrespective of the distance between the sample and the MS inlet (FIG. 13).

Figure 14:
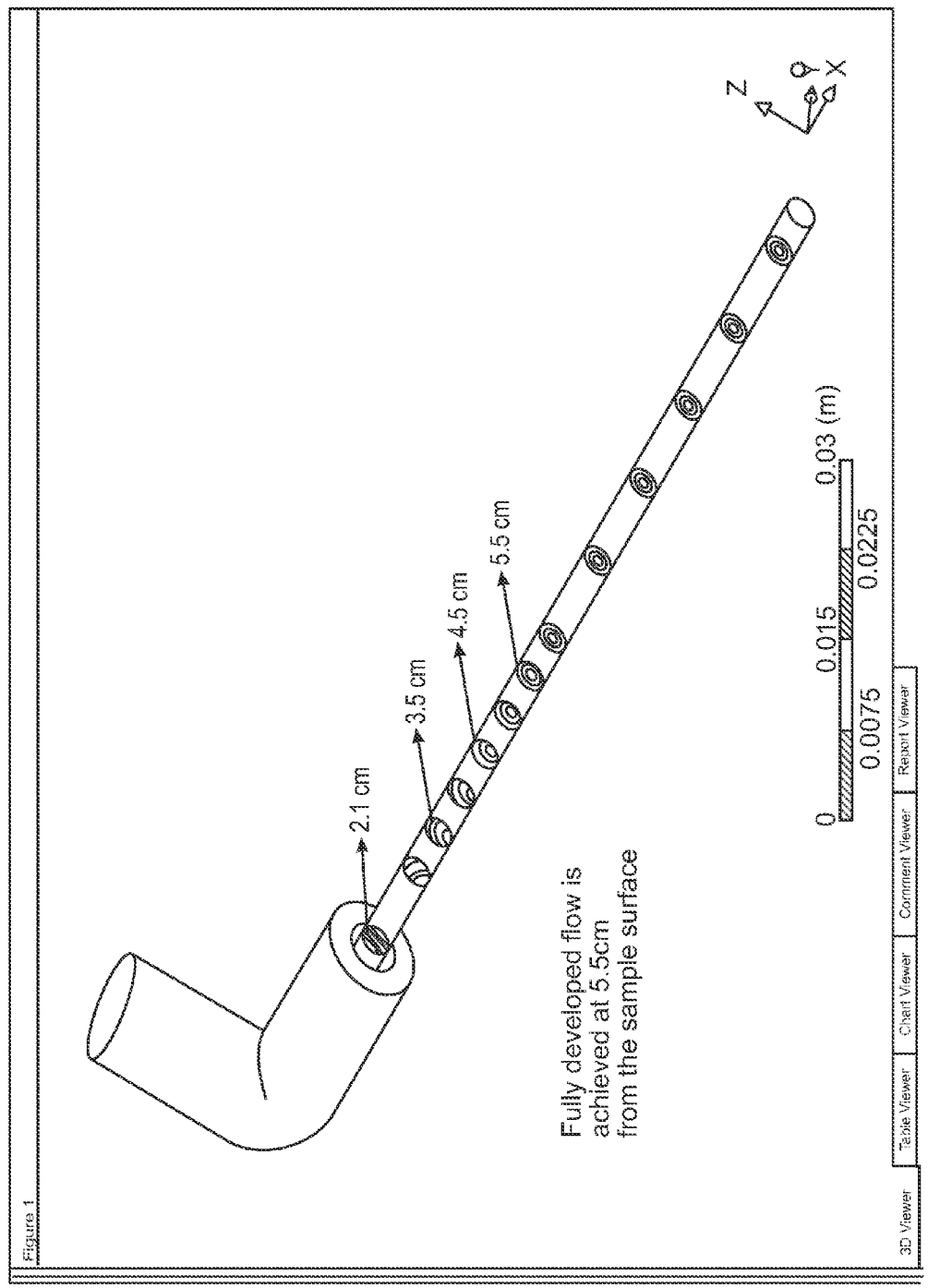
FIG. 14 is a diagram showing a CFD simulation, indicating fully developed laminar flow is achieved at around 55 mm.
Figure 21:
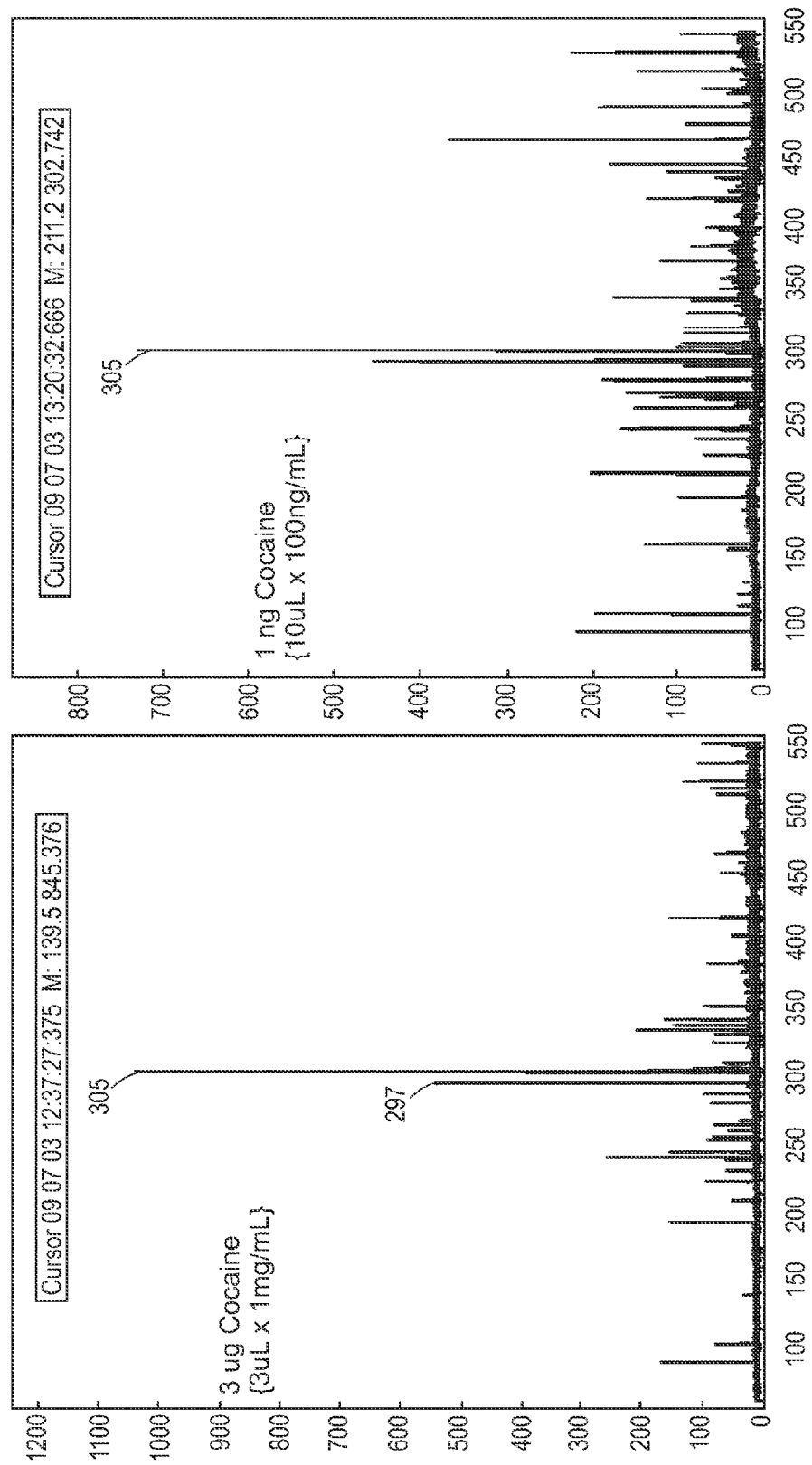
FIG. 21 is a set of mass spectra showing cocaine detected on a Mini 10 instrument with a DESI focusing source.

Without being limited by any particular theory or mechanism of action, it is believed that the stable level was reached due to the inception of a fully developed laminar flow a certain distance downstream of the drift tube. Once the fully developed flow regime was achieved, the ions were focused to the center of the ion transfer member and were transmitted to the inlet of the mass spectrometer without any loss. Diffusion loss of ions was low. Hence, beyond a certain distance the loss of ions was very low. This technique of flow focusing using a 10 cm drift tube of 0.24" ID was also demonstrated with the Mini 10 instrument (See FIG. 21). Using a commercial CFD package (Ansys CFX), the flow evolution in the drift tube due to the DESI spray was calculated. It was found that the fully developed laminar flow regime was achieved in the drift tube at about the same distance beyond which the signal fall of rate was found to be low. (See FIG. 14).

Figure 15:
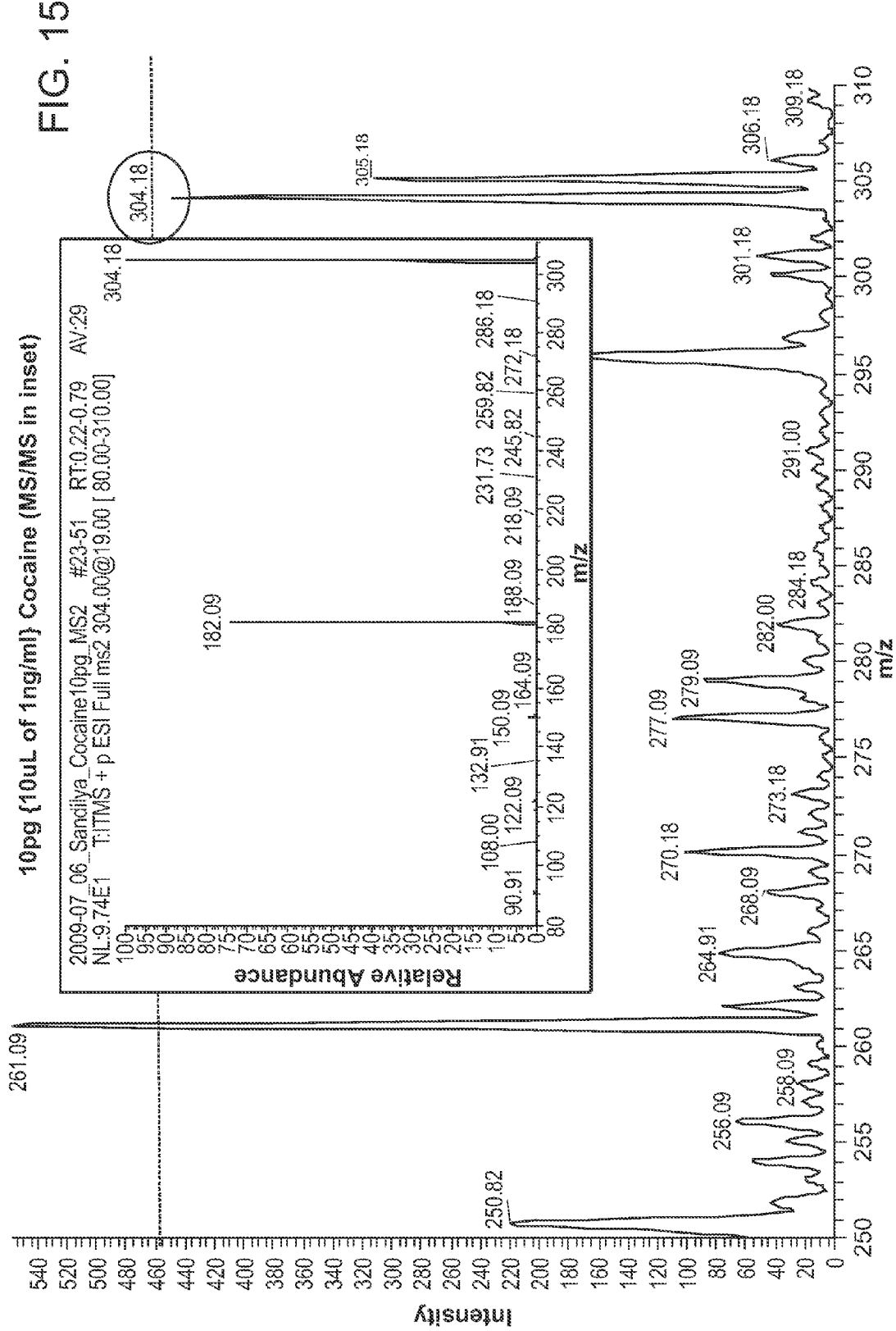
FIG. 15 is a mass spectrum of 10 pg of cocaine detected on a glass slide, 10 cm away from the MS inlet using the device shown in FIG. 12. The MS/MS spectrum is shown in the inset. An LTQ (Thermo Fisher Scientific) mass spectrometer was used
Figure 16:
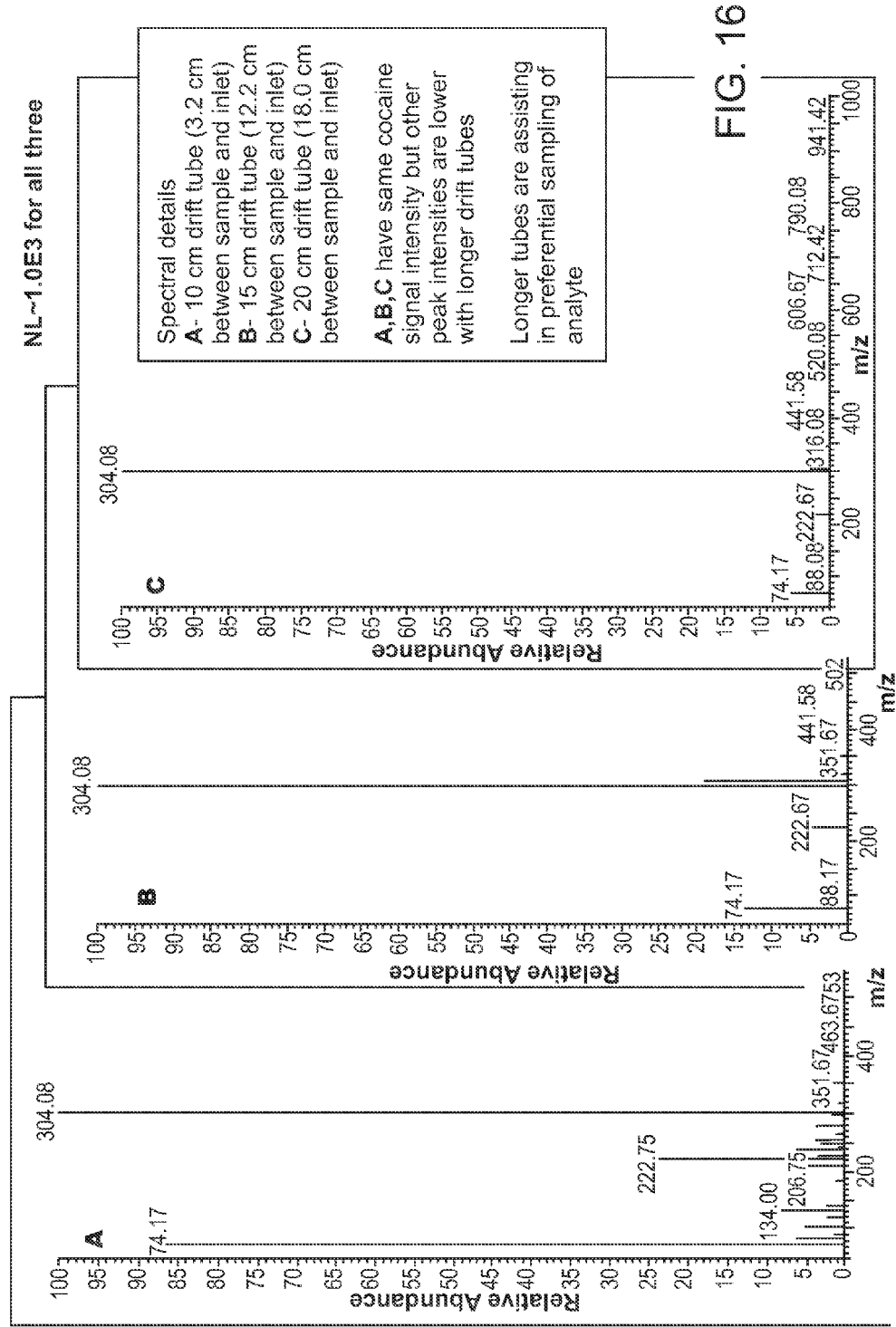
FIG. 16 is a set of mass spectra for different drift tubes showing differences in relative intensities of analyte vs. background signal intensities. Spectra were collected using the device shown in FIG. 12 and an LTQ mass spectrometer
Figure 20:
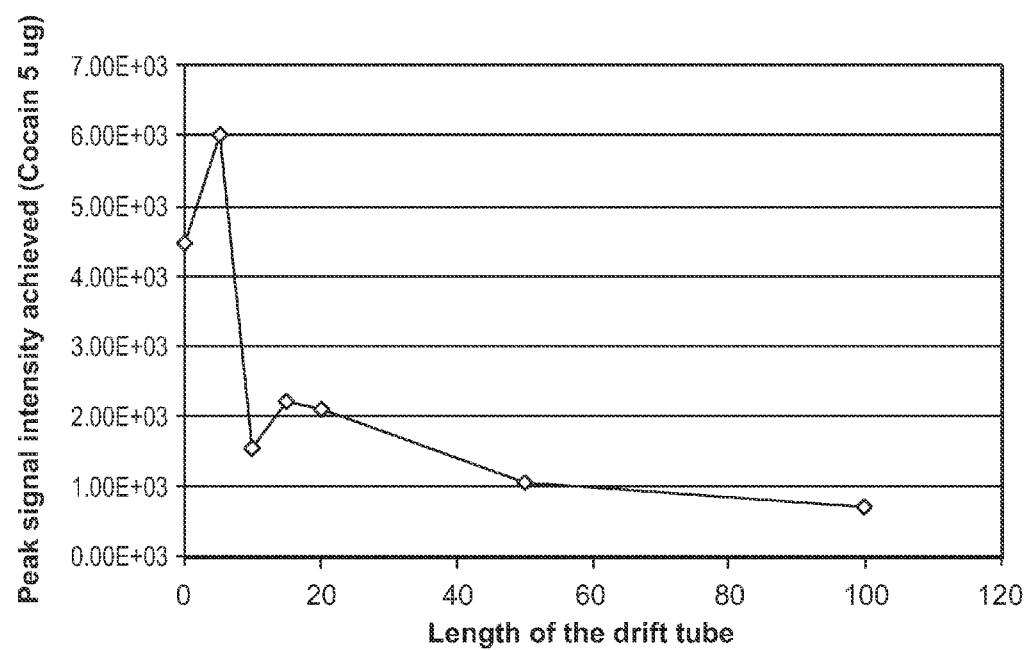
FIG. 20 is a graph showing peak signal intensities achieved with each transfer tube in DESI configuration.

Different drift tube lengths were used to collect spectrum of cocaine and the corresponding peak intensities were compared. Signal intensities with 5 cm, 10 cm, 15 cm, 20 cm, 50 cm, and 100 cm transfer tubes were recorded using an LTQ mass spectrometer (Thermo Fisher Scientific, Inc.). The peak signal intensity achieved with each of the transfer tube was plotted (See FIG. 20). These data show that the fall in signal with increased sampling distance was not very significant. This is due to laminar flow focusing of ions and consequent efficient transport. With a 10 cm transfer tube, a very good signal for 10 µg of cocaine on a glass slide was detected with potential for even a 10 times lower detection limit (FIG. 15). It was observed that the relative intensity of the background peaks were lower for longer transfer tubes (FIG. 16). It was concluded that a longer drift tube filtered out background ions more efficiently than a shorter drift tube, and thus a longer drift tube assisted in obtaining the ions of interest from the sample. This was akin to pre-concentration and selective analyte sampling (Cotte-Rodríguez et al, Chem. Commun., 2006, 2968-2970).

Example 5

Large Area

Figure 17:
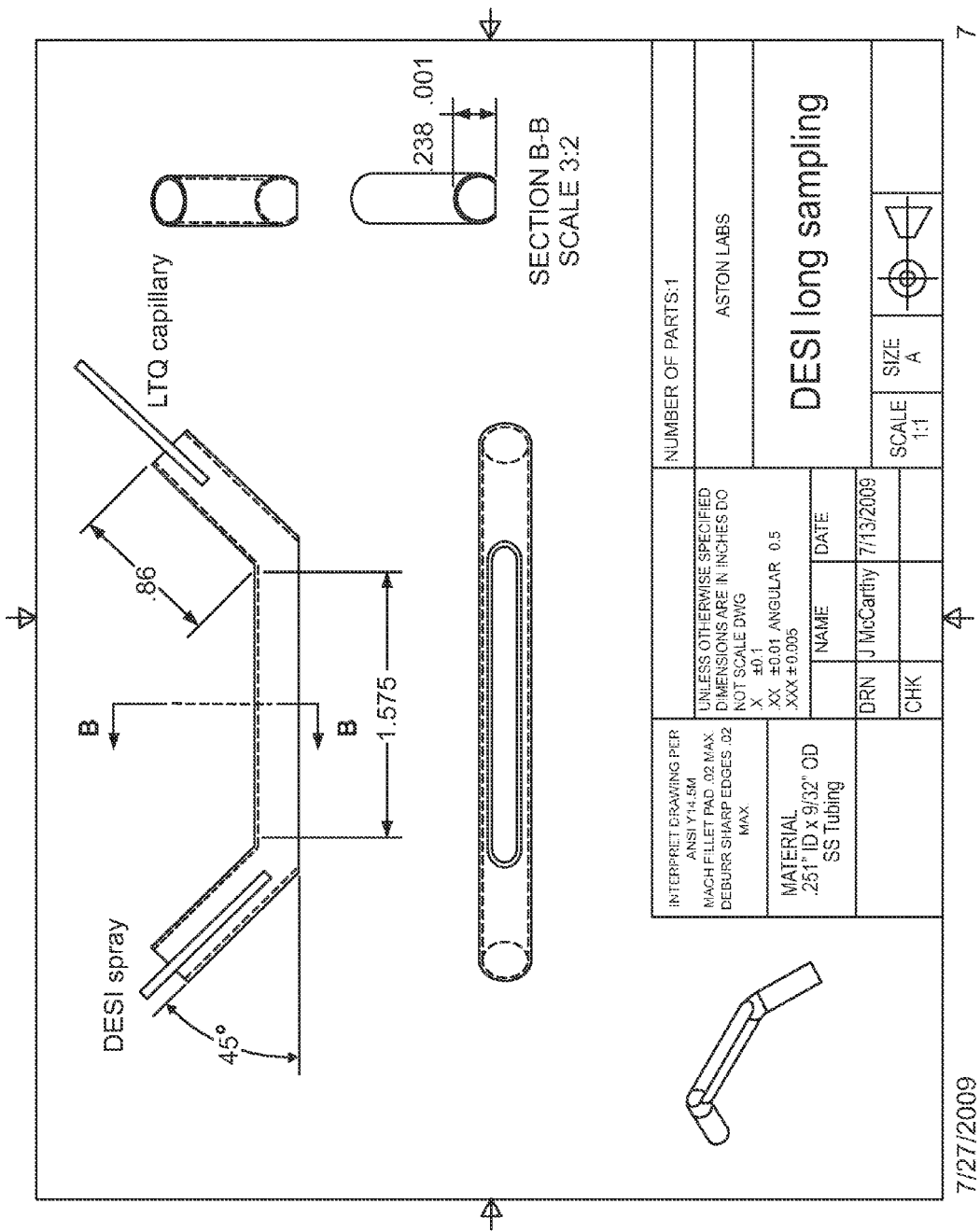
FIG. 17 is a schematic of the large area sampling configuration with a DESI source.

For the DESI configuration, a large area analysis was made by re-designing the drift tube and the sampling area. To increase the sampling area, a quarter inch tube was bent at a 45° angle at two sides, leaving a 4 cm central straight tube. The bottom of this portion was cut to create a sampling area. The schematic and drawing are shown in FIG. 17. The new sampling surface had a 4 cm×3.5 mm sampling area. A thin sampling area was used to allow for a confined area for gas flow. In the DESI configuration, as external pump was not used to assist transfer of ions, rather the DESI gas jet was used to transport the ions through a narrow area for ensuring laminar flow development.

Figure 18:
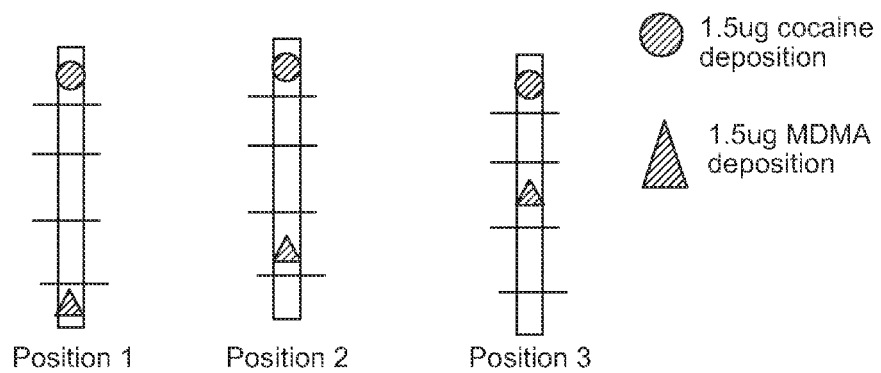
FIG. 18 is a diagram showing a configuration of an experiment with a large area sampling DESI source.
Figure 19:
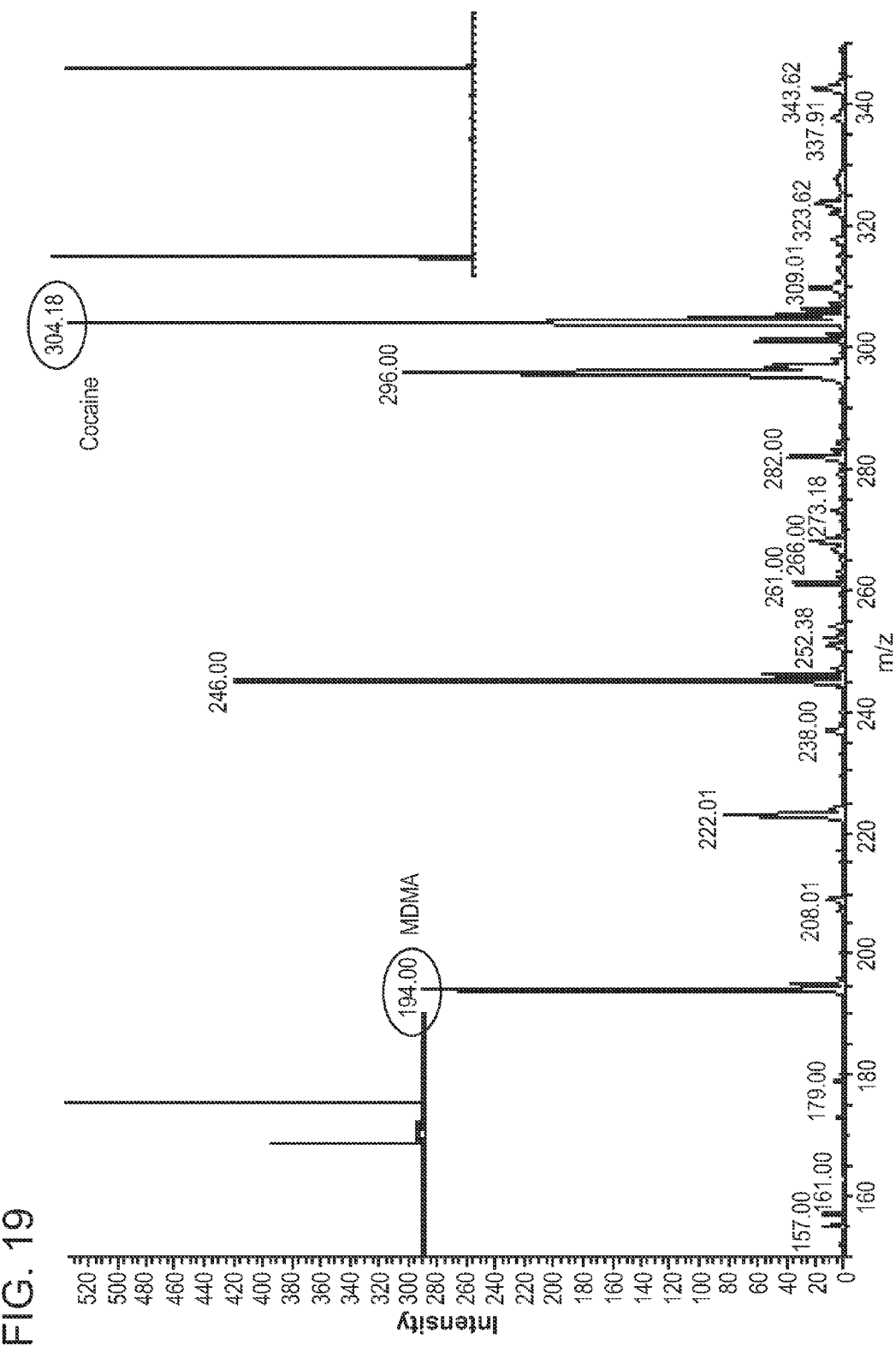
FIG. 19 is a mass spectrum corresponding to position 1 for a large area sampling DESI source.

The effect of position of analyte in the sampling region on signal intensity was tested. Two analytes, MDMA (3,4-Methylenedioxymethamphetamine), and cocaine were used. The cocaine position was fixed as shown by a circular shape and MDMA by triangle. Cocaine was closer to the DESI spray end. MDMA was closer to the MS sampling inlet. The pictorial representation of the experiment performed is shown in FIG. 18. Data show that the system was able to distinctly detect both the cocaine and the MDMA of 1.5 µg (See mass spectra of FIG. 19).

Example 6

Long Distance Ion Transfer—Low Temperature Plasma (LTP)

Mass spectrometers typically rely on the vacuum pumps of the system to generate a vacuum to pull ions into the system that are generated from an ambient ionization source. This is problematic with a miniature mass spectrometer because the vacuum pumps of such systems are much less powerful than those of standard mass spectrometer systems. It is particularly difficult to couple an ambient ionization source with a miniature mass spectrometer due to the decreased vacuum power of such an instrument. Systems of the invention generate an enlarged gas flow that increases efficiency of the movement of ions, and thus provides for efficient and focused transfer of ions generated from an ambient ionization source and transfer to an inlet of a miniature mass spectrometer.

Figure 22:
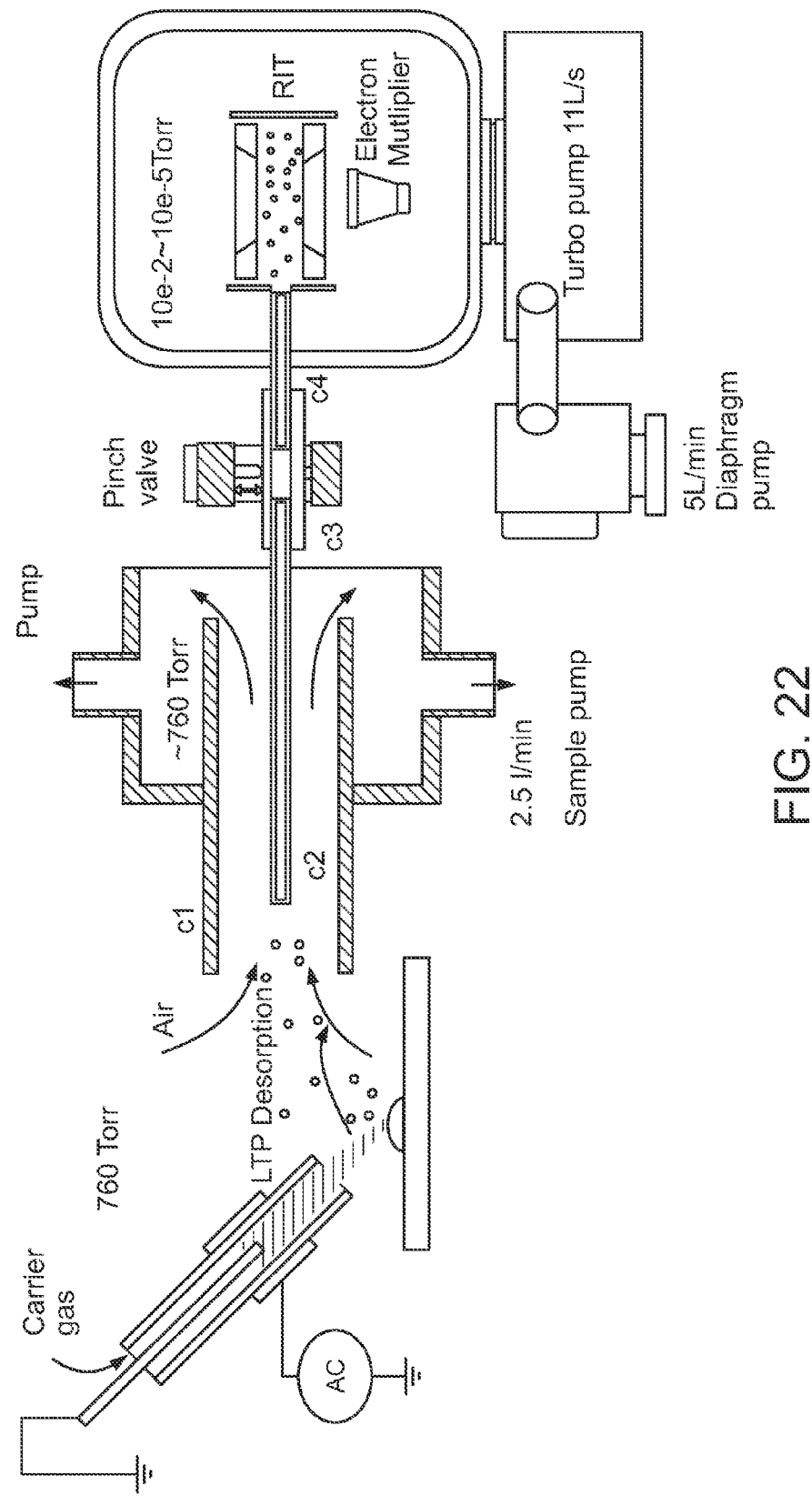
FIG. 22 is a schematic diagram of showing an LTP probe and a miniature mass spectrometer with a discontinuous atmospheric pressure interface coupled through an ion transfer member and a gas flow generating device.
Figure 23B:
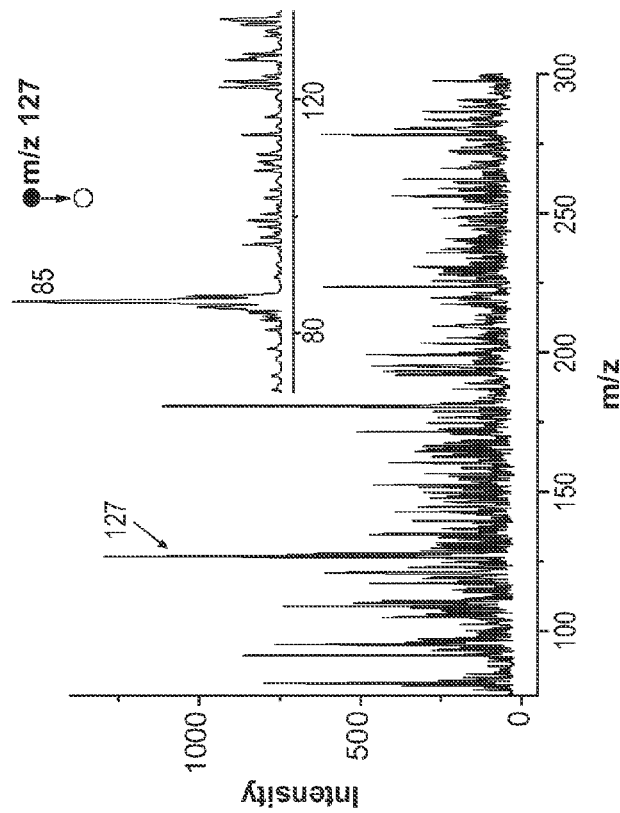
FIGS. 23A-D shows a typical spectra of melamine in different matrices using LTP/Mini 10.5.
Figure 23A:
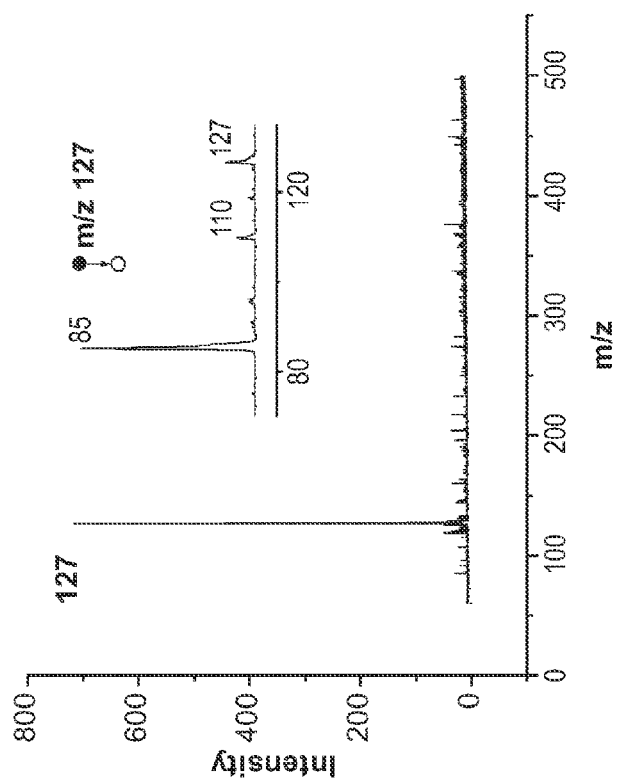
Figure 23D:
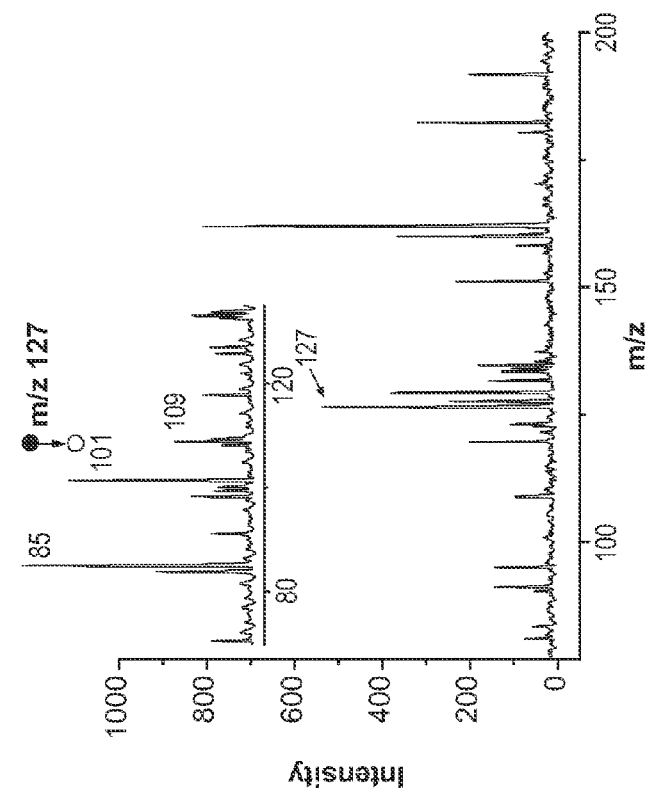
Figure 23C:
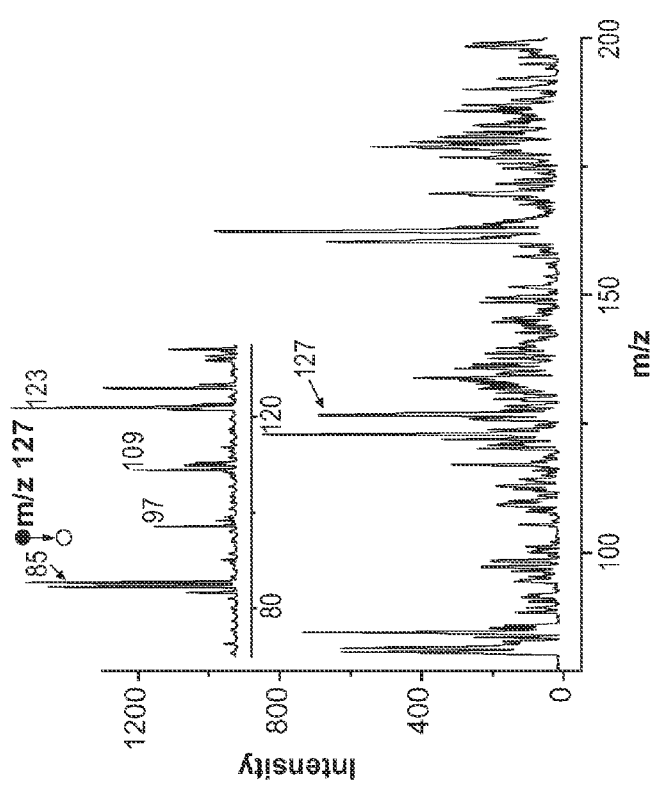

A low temperature plasma (LTP) ambient ionization source, coupled with a portable mass spectrometer (Mini 10.5), was used for the determination of melamine contamination in whole milk and related products (FIG. 22). Thermally assisted desorption and ionization of the analyte was achieved with the LTP probe. The small size, low power consumption and capability for direct sampling without pretreatment, makes LTP an appropriate ionization method for use in conjunction with a handheld mass spectrometer. The standard discontinuous atmospheric pressure interface used to connect atmospheric pressure ion sources to mini mass spectrometers (Gao et al. *Analytical Chemistry*, 2008, 80, 4026-4032) was coupled with an ion transfer member with supplementary pumping to increase the ion transfer efficiency. Whole milk, fish, milk powder and other complex matrices spiked with melamine were placed on the glass slide close to the vacuum inlet and analyzed without sample pretreatment. Analysis rates of two samples per minute were achieved while levels of melamine as low as 250 ng/mL were detected in whole milk with a linear dynamic range of 0.5-50 µg/mL and a relative standard deviation of 7.6%~16.2% (FIG. 23).

What is claimed is:

1. A system for analyzing a sample, the system comprising:
   an ionizing source for converting molecules of a sample into sample ions;
   an ion analysis device;
   a pump external to the ion analysis device;
   an ion transfer member external the ion analysis device, wherein the pump facilitates collection of the sample ions in the ion transfer member that is external the ion analysis device, which sample ions are transferred through the ion transfer member to an inlet of the ion analysis device.

2. The system according to claim 1, wherein the pump produces a laminar gas flow without regions of recirculation that transfers the sample ions through the ion transfer member to the inlet of the ion analysis device.

3. The system according to claim 1, wherein the ionizing source comprises a gas inlet port and an electrode positioned within the source to interact with a gas introduced through the gas inlet port and to generate a discharge that interacts with the sample to produce the sample ions.

4. The system according to claim 1, wherein the sample ions are produced in a region at about atmospheric pressure.

5. The system according to claim 1, wherein the ion transfer member is a tube.

6. The system according to claim 5, wherein the tube is composed of a rigid material.

7. The system according to claim 6, wherein the rigid material is metal or glass.

8. The system according to claim 5, wherein the tube is straight.

9. The system according to claim 1, wherein the ionizing source is selected from the group consisting of: an electrospray ionization source, a nano-electrospray ionization source, an atmospheric pressure matrix-assisted laser desorption ionization source, an atmospheric pressure chemical ionization source, a desorption electrospray ionization source, an atmospheric pressure dielectric barrier discharge ionization source, an atmospheric pressure low temperature plasma desorption ionization source, and an electrospray-assisted laser desorption ionization source.

10. The system according to claim 1, wherein the ion analysis device is selected from the group consisting of a mass spectrometer, a handheld mass spectrometer, and an ion mobility ion analysis device.

11. The system according to claim 10, wherein the mass spectrometer is selected from the group consisting of: a quadrupole ion trap, a rectilinear ion trap, a cylindrical ion trap, a ion cyclotron resonance trap, an orbitrap, a sector, and a time of flight mass spectrometer.

12. The system according to claim 1, further comprising a sample stage configured to
   hold the sample.

13. The system according to claim 12, wherein the ionizing source is arranged such that
   a distal tip of the ionizing source is pointed at the sample stage.

14. A system for analyzing a sample, the system comprising:
- a sample stage configured to hold a sample;
- an ionizing source arranged such that a distal tip of the ionizing source is pointed at the sample stage so that sample ions are generated from the sample;
- an ion analysis device;
- a pump external to the ion analysis device; and
- an ion transfer member external the ion analysis device, wherein the pump facilitates collection of the sample ions in the ion transfer member that is external the ion analysis device, which sample ions are transferred through the ion transfer member to an inlet of the ion analysis device.

15. The system according to claim 14, wherein the ionizing source comprises a gas inlet port and an electrode positioned within the source to interact with a gas introduced through the gas inlet port and to generate a discharge that interacts with the sample to produce the sample ions.

16. The system according to claim 14, wherein the sample ions are produced in a region at about atmospheric pressure.

17. The system according to claim 14, wherein the ion transfer member is a tube.

18. The system according to claim 17, wherein the tube is composed of a rigid material.

19. The system according to claim 18, wherein the rigid material is metal or glass.

* * * * *